US008598215B2

(12) United States Patent
Lee

(10) Patent No.: US 8,598,215 B2
(45) Date of Patent: Dec. 3, 2013

(54) COMBINATION OF EPOTHILONE ANALOGS AND CHEMOTHERAPEUTIC AGENTS FOR THE TREATMENT OF PROLIFERATIVE DISEASES

(75) Inventor: Francis Y. F. Lee, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1106 days.

(21) Appl. No.: 12/508,100

(22) Filed: Jul. 23, 2009

(65) Prior Publication Data

US 2010/0015149 A1  Jan. 21, 2010

Related U.S. Application Data

(62) Division of application No. 10/850,072, filed on May 20, 2004, which is a division of application No. 10/091,061, filed on Mar. 5, 2002, now Pat. No. 7,312,237.

(60) Provisional application No. 60/275,801, filed on Mar. 14, 2001, provisional application No. 60/316,395, filed on Aug. 31, 2001.

(51) Int. Cl.
*A01N 43/78* (2006.01)
*A01N 43/20* (2006.01)
*A01N 43/24* (2006.01)
*A61K 31/425* (2006.01)
*A61K 31/335* (2006.01)

(52) U.S. Cl.
USPC ............ 514/365; 514/366; 514/475; 514/183

(58) Field of Classification Search
USPC .................................. 514/365, 366, 475, 183
See application file for complete search history.

(56) References Cited

U.S. PATENT DOCUMENTS

| | | | |
|---|---|---|---|
| 5,728,687 A | 3/1998 | Bissery | |
| 6,162,804 A | 12/2000 | Bilodeau et al. | |
| 6,194,181 B1 | 2/2001 | Hofmann et al. | |
| 6,204,388 B1 | 3/2001 | Danishefsky et al. | |
| 6,211,412 B1 | 4/2001 | Georg et al. | |
| 6,262,094 B1 | 7/2001 | Hoefle et al. | |
| 6,262,096 B1 | 7/2001 | Kim et al. | |
| 6,326,390 B1 * | 12/2001 | Leung et al. ................ | 514/383 |
| 6,365,749 B1 | 4/2002 | Kim et al. | |
| 6,380,395 B1 | 4/2002 | Vite et al. | |
| 6,399,638 B1 | 6/2002 | Vite et al. | |
| 6,441,026 B1 | 8/2002 | Bissery | |
| 6,441,186 B1 | 8/2002 | Nicolaou et al. | |
| 6,462,017 B1 | 10/2002 | Rudolph et al. | |
| 6,498,257 B1 | 12/2002 | Vite et al. | |
| 6,537,988 B2 | 3/2003 | Lee | |
| 6,548,531 B2 | 4/2003 | Breimer et al. | |
| 6,576,651 B2 | 6/2003 | Bandyopadhyay et al. | |
| 6,586,428 B2 | 7/2003 | Geroni et al. | |
| 6,593,115 B2 | 7/2003 | Vite et al. | |
| 6,605,599 B1 | 8/2003 | Vite et al. | |
| 6,670,384 B2 | 12/2003 | Bandyopadhyay et al. | |
| 6,686,380 B2 | 2/2004 | Lee | |
| 6,689,802 B2 | 2/2004 | DiMarco et al. | |
| 6,727,276 B2 | 4/2004 | Lee | |
| 6,780,620 B1 | 8/2004 | Li et al. | |
| 6,822,001 B2 | 11/2004 | Schwendner et al. | |
| 6,831,090 B2 | 12/2004 | Vite et al. | |
| 6,867,305 B2 * | 3/2005 | Danishefsky et al. ........ | 548/204 |
| 6,982,265 B1 | 1/2006 | Hunt et al. | |
| 7,022,330 B2 | 4/2006 | Bandyopadhyay et al. | |
| 2002/0156110 A1 | 10/2002 | Arslanian et al. | |
| 2002/0198216 A1 | 12/2002 | Njoroge et al. | |
| 2003/0191162 A1 | 10/2003 | Langecker et al. | |
| 2004/0023925 A1 | 2/2004 | Chang et al. | |
| 2008/0119529 A1 | 5/2008 | Chen et al. | |

FOREIGN PATENT DOCUMENTS

| | | |
|---|---|---|
| DE | 41 38 042 | 5/1993 |
| DE | 195 42 986 | 5/1997 |
| DE | 196 36 343 | 10/1997 |
| DE | 196 39 456 | 3/1998 |
| DE | 196 45 361 | 4/1998 |
| DE | 196 45 362 | 4/1998 |
| DE | 196 47 580 | 5/1998 |
| DE | 197 01 758 | 7/1998 |
| DE | 197 07 505 | 9/1998 |
| DE | 197 13 970 | 10/1998 |
| DE | 197 20 312 | 11/1998 |
| DE | 198 21 954 | 11/1998 |
| DE | 197 26 627 | 12/1998 |
| EP | 0 879 605 | 11/1998 |
| WO | WO 93/10121 | 5/1993 |
| WO | WO 97/19086 | 5/1997 |
| WO | WO 98/08849 | 3/1998 |
| WO | WO 98/22461 | 5/1998 |
| WO | WO 98/24427 | 6/1998 |

(Continued)

OTHER PUBLICATIONS

Altmann, K.-H. et al., "Epothilones and related structures—a new class of microtubule inhibitors with potent in vivo antitumor activity", Biochimica et Biophysica Acta, vol. 1470, pp. M79-M91 (2000).
Baker, S.D., "Drug Interactions with the Taxanes", Pharmacotherapy, vol. 17, No. 5, Pt. 2, pp. 126S-132S (1997).
Balog, A. et al., "Total Synthesis of (—)-Epothilone A", Angew. Chem. Int. Ed. Engl., vol. 35, No. 23/24, pp. 2801-2803 (1996).
Baselga, J. et al., "Phase I Studies of Anti-Epidermal Growth Factor Receptor Chimeric Antibody C225 Alone and in Combination with Cisplatin", Journal of Clinical Oncology, vol. 18, No. 4, pp. 904-914 (2000).
Bertinato, P. et al., "Studies Toward a Synthesis of Epothilone A: Stereocontrolled Assembly of the Acyl Region and Models for Macrocyclization", J. Org. Chem. vol. 61, No. 23, pp. 8000-8001 (1996).

(Continued)

*Primary Examiner* — Yong Chong
(74) *Attorney, Agent, or Firm* — Hong Liu

(57) ABSTRACT

Compositions and methods are disclosed which are useful of the treatment and prevention of proliferative disorders.

5 Claims, 8 Drawing Sheets

(56) References Cited

FOREIGN PATENT DOCUMENTS

| WO | WO 98/25929 | 6/1998 |
|---|---|---|
| WO | WO 98/38192 | 9/1998 |
| WO | WO 98/47891 | 10/1998 |
| WO | WO 99/01124 | 1/1999 |
| WO | WO 99/02514 | 1/1999 |
| WO | WO 99/03848 | 1/1999 |
| WO | WO 99/07692 | 2/1999 |
| WO | WO 99/27890 | 6/1999 |
| WO | WO 99/39694 | 8/1999 |
| WO | WO 99/42602 | 8/1999 |
| WO | WO 99/43320 | 9/1999 |
| WO | WO 99/43653 | 9/1999 |
| WO | WO 99/54319 | 10/1999 |
| WO | WO 99/67252 | 12/1999 |
| WO | WO 00/00485 | 1/2000 |
| WO | WO 00/31247 | 6/2000 |
| WO | WO 00/37473 | 6/2000 |
| WO | WO 00/38519 | 7/2000 |
| WO | WO 00/38730 | 7/2000 |
| WO | WO 00/49021 | 8/2000 |
| WO | WO 0050423 | 8/2000 |
| WO | WO 00/66589 | 11/2000 |
| WO | WO 01/07082 | 2/2001 |
| WO | WO 01/34133 | 5/2001 |
| WO | WO 01/49287 | 7/2001 |
| WO | WO 01/64650 | 9/2001 |
| WO | WO 01/82949 | 11/2001 |
| WO | WO 02/39958 | 5/2002 |
| WO | WO 02/057217 | 7/2002 |
| WO | WO 02/067941 | 9/2002 |
| WO | WO 02/074042 | 9/2002 |
| WO | WO 02/089824 | 11/2002 |
| WO | WO 03/007924 | 1/2003 |
| WO | WO 03/057217 | 7/2003 |

OTHER PUBLICATIONS

Bertini, F. et al., "Alkenes from Epoxides by Reductive Elimination with Magnesium Bromide-Magnesium Amalgam", Chemical Communications, p. 144 (1970).

Bissery, M.C. et al., "Preclinical In Vivo Activity of Docetaxel-Containing Combinations", Proceedings of ASCO, vol. 14, No. 1599, p. 489 (1995).

BisSery, M.-C. et al., "Preclinical Profile of Docetaxel (Taxotere): Efficacy as a Single Agent and in Combination", Seminars in Oncology, vol. 22, No. 6, Suppl. 13, pp. 3-16 (1995).

Bollag, D.M., "Epothilones: novel microtubule-stabilising agents", Exp. Opin. Invest. Drugs., vol. 6, No. 7, pp. 867-873 (1997).

Bollag, D.M. et al., "Epothilone, a new structural class of microtubule stabilizer", Proceedings of the American Association for Cancer Research, vol. 36, No. 2711, p. 454 (1995).

Bollag, D.M. et al., "Epothilones, a New Class of Microtubule-stabilizing Agents with a Taxol-like Mechanism of Action", Cancer Research, vol. 55, pp. 2325-2333 (1995).

Borman, S., "Epothilone Epiphany: Total Syntheses", Chemical & Engineering News, vol. 74, No. 52, pp. 24-26 (1996).

Chemical & Engineering News, "First total synthesis of epothilone B", vol. 75, No. 13, p. 23 (1997).

Chemical & Engineering News, "Solid-phase epothilone synthesis used to create analog library", vol. 75, No. 20, p. 33 (1997).

Claus, E. et al., "Synthesis of the C1-C9 Segment of Epothilons", Tetrahedron Letters, vol. 38, No. 8, pp. 1359-1362 (1997).

De Brabander, J. et al., "Towards a Synthesis of Epothilone A: Rapid Assembly of the C1-C6 and C7-C12 Fragments", Synlett, No. 7, pp. 824-826 (1997).

Fujisawa, T. et al., "Deoxygenation of Epoxides to Olefins with $FeCl_3$—BuLi System", Chemistry Letters, pp. 883-886 (1974).

Fujiwara, Y. et al., "Reductive Coupling of Carbonyl Compounds to Olefins by Tungsten Hexachloride-Lithium Aluminum Hydride and Some Tungsten and Molybdenum Carbonyls", J. Org. Chem., vol. 43, No. 12, pp. 2477-2479 (1978).

Gabriel, T. et al., "The Chromium-Reformatsky Reaction: Asymmetric Synthesis of the Aldol Fragment of the Cytotoxic Epothilons from 3-(2-Bromoacyl)-2-oxazolidinones", Tetrahedron Letters, vol. 38, No. 8, pp. 1363-1366 (1997).

Gerth, K. et al., "Epothilons A and B: Antifungal and Cytotoxic Compounds from *Sorangium cellulosum* (Myxobacteria): Production, Physico-chemical and Biological Properties", The Journal of Antibiotics, vol. 49, No. 6, pp. 560-563 (1996).

Gladysz, J.A. et al., "Deoxygenation of Epoxides by Metal Atom Cocondensation", J. Org. Chem., vol. 41, No. 22, pp. 3647-3648 (1976).

Höfle, G. et al., "Epothilone A and B—Novel 16-Membered Macrolides with Cytotoxic Activity: Isolation, Crystal Structure, and Conformation in Solution", Angew. Chem. Int. Ed. Engl., vol. 35, No. 13/14, pp. 1567-1569 (1996).

Höfle, G. et al., "N-Oxidation of Epothilone A—C and O-Acyl Rearrangement to C-19- and C-21-Substituted Epothilones", Angew. Chem. Int. Ed., vol. 38, No. 13/14, pp. 1971-1974 (1999).

Holmes, F.A., "Paclitaxel Combination Therapy in the Treatment of Metastatic Breast Cancer", Seminars in Oncology, vol. 23, No. 5, Suppl. 12, pp. 29-39 (1996).

Hortobagyi, G.N. et al., "Paclitaxel-Containing Combination Chemotherapy for Metastatic Breast Cancer", Seminars in Oncology, vol. 23, No. 1, Suppl. 1, pp. 53-57 (1996).

Hunt, J.T. et al., "Discovery of (R)-7-Cyano-2,3,4,5-tetrahydro-1-(1H-imidazol-4-ylmethyl)-3-(phenylmethyl)-4-(2-thienylsulfonyl)-1H-1,4-benzodiazepine (BMS-214662), a Farnesyltransferase Inhibitor with Potent Preclinical Antitumor Activity", Journal of Medicinal Chemistry, vol. 43, No. 20, pp. 3589-3595 (2000).

Inokuchi, T. et al., "Opening of Epoxides to Olefins or Halohydrins with Vanadium(II)-Tetrahydrofuran or Vanadium(III)-Tetrahydrofuran Complexes", Synlett, No. 6, pp. 510-512 (1992).

Johnson, K. et al., "5-Fluorouracil interferes with taxol cytotoxicity on human solid tumor cells", Proceedings of the American Association for Cancer Research, vol. 38, No. 2162, p. 323 (1997).

Johnson, K.R. et al., "5-Fluorouracil Interferes with Paclitaxel Cytotoxicity against Human Solid Tumor Cells", Clinical Cancer Research, vol. 3, pp. 1739-1745 (1997).

Kano, Y. et al., "Schedule-dependent interaction between paclitaxel and 5-fluorouracil in human carcinoma cell lines in vitro", British Journal of Cancer, vol. 74, pp. 704-710 (1996).

Kearney, N. et al., "Herceptin®: implications for breast cancer management", European Journal of Oncology Nursing, vol. 4, Suppl. 1, pp. 37-41 (2000).

Kowalski, R.J. et al., "Activities of the Microtubule-stabilizing Agents Epothilones A and B with Purified Tubulin and in Cells Resistant to Paclitaxel (Taxol®)", The Journal of Biological Chemistry, vol. 272, No. 4, pp. 2534-2541 (1997).

Kupchan, S.M. et al., "Reductive Elimination of Epoxides to Olefins with Zinc-Copper Couple", J. Org. Chem., vol. 36, No. 9, pp. 1187-1190 (1971).

Marshall, A., "Total synthesis of epothilone", Nature Biotechnology, vol. 15, p. 205 (1997).

Martin, M.G. et al., "Epoxides as Alkene Protecting Groups. A Mild and Efficient Deoxygenation", Tetrahedron Letters, vol. 25, No. 3, pp. 251-254 (1984).

McMurry, J.E. et al., "Reduction of Epoxides to Olefins with Low Valent Titanium", J. Org. Chem., vol. 40, No. 17, pp. 2555-2556 (1975).

McMurry, J.E. et al., "Some Deoxygenation Reactions with Low-Valent Titanium ($TiCl_3/LiAlH_4$)", The Journal of Organic Chemistry, vol. 43, No. 17, pp. 3249-3254 (1978).

Meng, D. et al., "Remote Effects in Macrolide Formation through Ring-Forming Olefin Metathesis: An Application to the Synthesis of Fully Active Epothilone Congeners", J. Am. Chem. Soc., vol. 119, No. 11, pp. 2733-2734 (1997).

Meng, D. et al., "Studies Toward a Synthesis of Epothilone A: Use of Hydropyran Templates for the Management of Acyclic Stereochemical Relationships", J. Org. Chem., vol. 61, No. 23, pp. 7998-7999 (1996).

Meng, D. et al., "Total Syntheses of Epothilones A and B", J. Am. Chem. Soc., vol. 119, No. 42, pp. 10073-10092 (1997).

(56) References Cited

OTHER PUBLICATIONS

Mensching, S. et al., "Generation of Thiazoles by Column Dehydrogenation of Thiazolidines with $MnO_2$", Journal für Praktische Chemie, vol. 339, pp. 96-97 (1997).

Mulzer, J. et al., "Synthesis of the C(1)-C(9) Segment of the Cytotoxic Macrolides Epothilon A and B", Tetrahedron Letters, vol. 37, No. 51, pp. 9179-9182 (1996).

Nicolaou, K.C. et al., "An Approach to Epothilones Based on Olefin Metathesis", Angew. Chem. Int. Ed. Engl., vol. 35, No. 20, pp. 2399-2401 (1996).

Nicolaou, K.C. et al., "Chemical Biology of Epothilones", Angew. Chem. Int. Ed., vol. 37, pp. 2014-2045 (1998).

Nicolaou, K.C. et al., "Chemistry, biology and medicine of selected tubulin polymerizing agents", Pure Appl. Chem., vol. 71, No. 6, pp. 989-997 (1999).

Nicolaou, K.C. et al., "Designed Epothilones: Combinatorial Synthesis, Tubulin Assembly Properties, and Cytotoxic Action Against Taxol-Resistant Tumor Cells", Angew. Chem. Int. Ed. Engl., vol. 36, No. 19, pp. 2097-2103 (1997).

Nicolaou, K.C. et al., "Synthesis and biological properties of C12,13-cyclopropyl-epothilone A and related epothilones", Chemistry & Biology, vol. 5, No. 7, pp. 365-372 (1998).

Nicolaou, K.C. et al., "Synthesis of epothilones A and B in solid and solution phase", Nature, vol. 387, pp. 268-272 (1997).

Nicolaou, K.C. et al., "Synthesis of epothilones A and B in solid and solution phase" (correction to Nature, vol. 387, pp. 268-272 (1997)), Nature, vol. 390, p. 100 (1997).

Nicolaou, K.C. et al., "The Olefin Metathesis Approach to Epothilone A and Its Analogues", J. Am. Chem. Soc., vol. 119, No. 34, pp. 7960-7973 (1997).

Nicolaou, K.C. et al., "Total Syntheses of Epothilones A and B via a Macrolactonization-Based Strategy", J. Am. Chem. Soc., vol. 119, No. 34, pp. 7974-7991 (1997).

Nicolaou, K.C. et al., "Total Synthesis of Epothilone A: The Macrolactonization Approach", Angew. Chem. Int. Ed. Engl., vol. 36, No. 5, pp. 525-527 (1997).

Nicolaou, K.C. et al., "Total Synthesis of Epothilone E and Analogues with Modified Side Chains through the Stille Coupling Reaction", Angew. Chem. Int. Ed., vol. 37, No. 1/2, pp. 84-87 (1998).

Nicolaou, K.C. et al., "Total Synthesis of Epothilone E and Related Side-chain Modified Analogues via a Stille Coupling Based Strategy", Bioorganic & Medicinal Chemistry, vol. 7, pp. 665-697 (1999).

Nicolaou, K.C. et al., "Total Synthesis of Oxazole- and Cyclopropane-Containing Epothilone B Analogues by the Macrolactonization Approach", Chem. Eur. J., vol. 3, No. 12, pp. 1971-1986 (1997).

Raucher, S. et al., "Total Synthesis of (+)-Dihydrocostunolide via Tandem Cope-Claisen Rearrangement", J. Org. Chem., vol. 51, No. 26, pp. 5503-5505 (1986).

Saeki, T. et al., "Mechanism and possible biochemical modulation of capecitabine (Xeloda), a newly generated oral fluoropyrimidine," Gan To Kagaku Ryoho, vol. 26, No. 4, pp. 447-455 (1999) (English abstract).

Sato, M. et al., "Reduction of Organic Compounds with Low-Valent Niobium ($NbCl_5$/$NaAlH_4$)", Chemistry Letters, pp. 157-160 (1982).

Schinzer, D. et al., "Studies Towards the Total Synthesis of Epothilones: Asymmetric Synthesis of the Key Fragments", Chem. Eur. J., vol. 2, No. 11, pp. 1477-1482 (1996).

Schinzer, D. et al., "Syntheses of (—)-Epothilone B", Chem. Eur. J., vol. 5, No. 9, pp. 2492-2500 (1999).

Schinzer, D. et al., "Total Synthesis of (—)-Epothilone A", Angew. Chem. Int. Ed. Engl., vol. 36, No. 5, pp. 523-524 (1997).

Schinzer, D. et al., "Total Synthesis of (—)-Epothilone A", Chem. Eur. J., vol. 5, No. 9, pp. 2483-2491 (1999).

Schobert, R. et al., "Reduction and Isomerization of Oxiranes and α-Diazoketones by Various Early Transition Metallocenes", Synlett, No. 8, pp. 465-466 (1990).

Sharpless, K.B. et al., "Lower Valent Tungsten Halides. A New Class of Reagents for Deoxygenation of Organic Molecules", Journal of the American Chemical Society, vol. 94, No. 18, pp. 6538-6540 (1972).

Su, D.-S. et al., "Structure-Activity Relationships of the Epothilones and the First In Vivo Comparison with Paclitaxel", Angew. Chem. Int. Ed. Engl., vol. 36, No. 19, pp. 2093-2096 (1997).

Su, D.-S. et al., "Total Synthesis of (—)-Epothilone B: An Extension of the Suzuki Coupling Method and Insights into Structure-Activity Relationships of the Epothilones", Angew. Chem. Int. Ed. Engl., vol. 36, No. 7, pp. 757-759 (1997).

Taylor, R.E. et al., "Towards the Synthesis of Epothilone A: Enantioselective Preparation of the Thiazole Sidechain and Macrocyclic Ring Closure", Tetrahedron Letters, vol. 38, No. 12, pp. 2061-2064 (1997).

Victory, S.F. et al., "Relative Stereochemistry and Solution Conformation of the Novel Paclitaxel-Like Antimitotic Agent Epothilone A", Bioorganic & Medicinal Chemistry Letters, vol. 6, No. 7, pp. 893-898 (1996).

Winkler, J.D. et al., "A Model for the Taxol (Paclitaxel)/Epothilone Pharmacophore", Bioorganic & Medicinal Chemistry Letters, vol. 6, No. 24, pp. 2963-2966 (1996).

Winkler, U. et al., "Cytokine-Release Syndrome in Patients with B-Cell Chronic Lymphocytic Leukemia and High Lymphocyte Counts After Treatment with an Anti-CD20 Monoclonal Antibody (Rituximab, IDEC-C2B8)", Blood, vol. 94, No. 7, pp. 2217-2224 (1999).

Yang, Z. et al., "Total Synthesis of Epothilone A: The Olefin Metathesis Approach", Angew. Chem. Int. Ed. Engl., vol. 36, No. 1/2, pp. 166-168 (1997).

\* cited by examiner

COMBINATION OF EPOTHILONE ANALOGS AND CHEMOTHERAPEUTIC AGENTS FOR THE TREATMENT OF PROLIFERATIVE DISEASES

CROSS-REFERENCE TO RELATED APPLICATIONS

This application is a divisional of U.S. application Ser. No. 10/850,072, filed on May 20, 2004, which is a divisional of U.S. patent application Ser. No. 10/091,061, filed Mar. 5, 2002, now U.S. Pat. No. 7,312,237, which claims priority to provisional application Ser. Nos. 60/275,801, filed Mar. 14, 2001 and 60/316,395, filed Aug. 31, 2001, each incorporated herein by reference in its entirety.

FIELD OF THE INVENTION

This invention relates to the fields of oncology and improved chemotherapy regimens.

BACKGROUND OF THE INVENTION

The disclosure of each literature article and published patent document referred to herein is incorporated by reference herein in its entirety.

The National Cancer Institute has estimated that in the United States alone, 1 in 3 people will be struck with cancer during their lifetime. Moreover, approximately 50% to 60% of people contracting cancer will eventually succumb to the disease. The widespread occurrence of this disease underscores the need for improved anticancer regimens for the treatment of malignancy.

Due to the wide variety of cancers presently observed, numerous anticancer agents have been developed to destroy cancer within the body. These compounds are administered to cancer patients with the objective of destroying or otherwise inhibiting the growth of malignant cells while leaving normal, healthy cells undisturbed. Anticancer agents have been classified based upon their mechanism of action.

One type of chemotherapeutic is referred to as a metal coordination complex. It is believed this type of chemotherapeutic forms predominantly inter-strand DNA cross links in the nuclei of cells, thereby preventing cellular replication. As a result, tumor growth is initially repressed, and then reversed. Another type of chemotherapeutic is referred to as an alkylating agent. These compounds function by inserting foreign compositions or molecules into the DNA of dividing cancer cells. As a result of these foreign moieties, the normal functions of cancer cells are disrupted and proliferation is prevented. Another type of chemotherapeutic is an antineoplastic agent. This type of agent prevents, kills, or blocks the growth and spread of cancer cells. Still other types of anticancer agents include nonsteroidal aromastase inhibitors, bifunctional alkylating agents, etc.

Paclitaxel represents one of the major classes of antimicrotubule agents that promotes tubulin polymerization and, presumably, mitotic arrest during cell division. Taxol7 (paclitaxel) has been shown to have excellent antitumor activity in vivo and has been employed in the treatment of a variety of cancers, including breast, ovarian and lung cancer. Unfortunately, many tumors develop resistance to paclitaxel.

The present inventors have discovered epothilone analogs that act synergistically when used in combination with certain conventional chemotherapeutic agents. It is an object of the invention to provide efficacious combination chemotherapeutic treatment regimens wherein epothilone analogs are combined with other anti-neoplastic agents for the treatment of proliferative diseases.

SUMMARY OF THE INVENTION

The present invention provides a synergistic method for the treatment of anti-proliferative diseases, including cancer, which comprises administering to a mammalian specie in need thereof a synergistically, therapeutically effective amount of: (1) at least one anti-proliferative agent and (2) a compound of formula I wherein

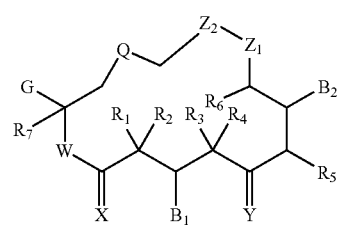

wherein:
Q is selected from the group consisting of

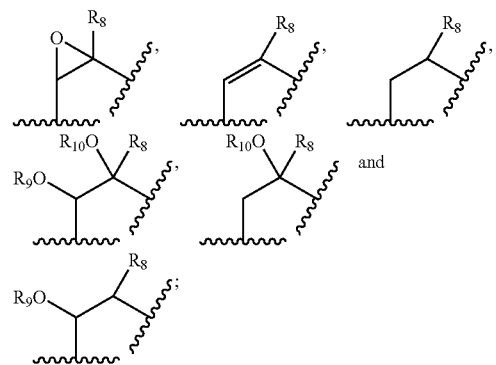

G is selected from the group consisting of alkyl, substituted alkyl, aryl, substituted aryl, heterocyclo,

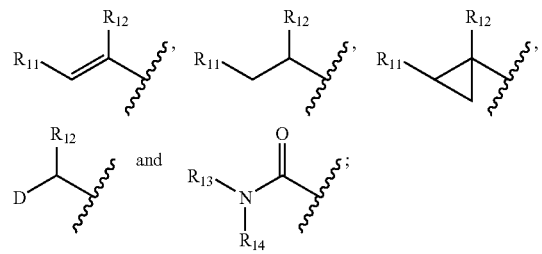

W is O or $NR_{15}$;
X is O or H, H;
Y is selected from the group consisting of O; H, $OR_{16}$; $OR_{17}$, $OR_{17}$; $NOR_{18}$; H, $NHOR_{19}$; H, $NR_{20}R_{21}$; H, H; and $CHR_{22}$; wherein $OR_{17}$, $OR_{17}$ can be a cyclic ketal;
$Z_1$ and $Z_2$ are independently selected from the group consisting of $CH_2$, O, $NR_{23}$, S, and $SO_2$, wherein only one of $Z_1$ and $Z_2$ can be a heteroatom;

$B_1$ and $B_2$ are independently selected from the group consisting of $OR_{24}$, $OCOR_{25}$, and $O-C(=O)-NR_{26}R_{27}$, and when $B_1$ is H and Y is OH, H, they can form a six-membered ring ketal or acetal;

D is selected from the group consisting of $NR_{28}R_{29}$, $NR_{30}COR_{31}$ and saturated heterocycle;

$R_1$, $R_2$, $R_3$, $R_4$, $R_5$, $R_6$, $R_7$, $R_{13}$, $R_{14}$, $R_{18}$, $R_{19}$, $R_{20}$, $R_{21}$, $R_{22}$, $R_{26}$ and $R_{27}$ are independently selected from the group consisting of H, alkyl, substituted alkyl, and aryl, and when $R_1$ and $R_2$ are alkyl can be joined to form a cycloalkyl, and when $R_3$ and $R_4$ are alkyl can be joined to form a cycloalkyl;

$R_9$, $R_{10}$, $R_{16}$, $R_{17}$, $R_{24}$, $R_{25}$ and $R_{31}$ are independently selected from the group consisting of H, alkyl, and substituted alkyl;

$R_8$, $R_{11}$, $R_{12}$, $R_{28}$, $R_{30}$, $R_{32}$, and $R_{33}$ are independently selected from the group consisting of H, alkyl, substituted alkyl, aryl, substituted aryl, cycloalkyl and heterocyclo;

$R_{15}$, $R_{23}$ and $R_{29}$ are independently selected from the group consisting of H, alkyl, substituted alkyl, aryl, substituted aryl, cycloalkyl, heterocyclo, $R_{32}C=O$, $R_{33}SO_2$, hydroxy, O-alkyl or O-substituted alkyl; and pharmaceutically acceptable salts thereof and any hydrates, solvates or geometric, optical and stereoisomers thereof;

with the proviso that compounds wherein

W and X are both O; and $R_1$, $R_2$ and $R_7$ are H; and $R_3$, $R_4$ and $R_6$ are methyl; and $R_8$ is H or methyl; and $Z_1$ and $Z_2$ are $CH_2$; and G is 1-methyl-2-(substituted-4-thiazolyl)ethenyl; and Q is as defined above are excluded.

Formula II provides another example of an epothilone suitable for use in the methods and compositions of the present invention:

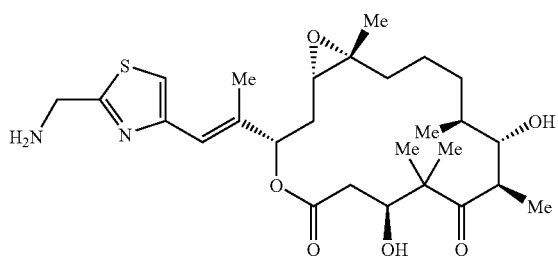 [SMILES: C/C(=C\c1csc(CN)n1)[C@@H]1C[C@@H]2O[C@]2(C)CCC[C@H](C)[C@H](O)[C@@H](C)C(=O)C(C)(C)[C@@H](O)CC(=O)O1]

where:

P-Q is a C, C double bond or an epoxide;

G is

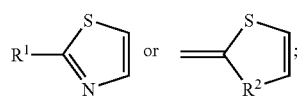

R is selected from the group of H, alkyl, and substituted alkyl;

$R^1$ is selected from the group consisting of

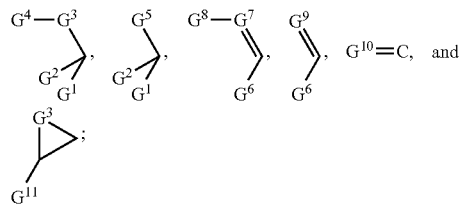

$R^2$ is

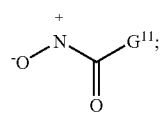

$G^1$ is selected from the group of H, halogen, CN, alkyl and substituted alkyl;

$G^2$ is selected from the group of H, alkyl, and substituted alkyl;

$G^3$ is selected from the group of O, S, and $NZ^1$;

$G^4$ is selected from the group of H, alkyl, substituted alkyl, $OZ^2$, $NZ^2Z^3$, $Z^2C=O$, $Z^4$ $SO_2$, and optionally substituted glycosyl;

$G^5$ is selected from the group of halogen, $N_3$, NCS, SH, CN, NC, $N(Z^1)_3^+$ and heteroaryl;

$G^6$ is selected from the group of H, alkyl, substituted alkyl, $CF_3$, $OZ^5$, $SZ^5$, and $NZ^5Z^6$;

$G^7$ is $CZ^7$ or N;

$G^8$ is selected from the group of H, halogen, alkyl, substituted alkyl, $OZ^{10}$, $SZ^{10}$, $NZ^{10}Z^{11}$;

$G^9$ is selected from the group of O, S, —NH—NH— and —N=N—;

$G^{10}$ is N or $CZ^{12}$;

$G^{11}$ is selected from the group of $H_2N$, substituted $H_2N$, alkyl, substituted alkyl, aryl, and substituted aryl;

$Z^1$, $Z^6$, $Z^9$, and $Z^{11}$ are independently selected from the group H, alkyl, substituted alkyl, acyl, and substituted acyl;

$Z^2$ is selected from the group of H, alkyl, substituted alkyl, aryl, substituted aryl, and heterocycle;

$Z^3$, $Z^5$, $Z^8$, and $Z^{10}$ are independently selected from the group H, alkyl, substituted alkyl, acyl, substituted acyl, aryl, and substituted aryl;

$Z^4$ is selected from the group of alkyl, substituted alkyl, aryl, substituted aryl, and heterocycle;

$Z^7$ is selected from the group of H, halogen, alkyl, substituted alkyl, aryl, substituted aryl, $OZ^8$, $SZ^8$, and $NZ^8Z^9$; and $Z^{12}$ is selected from the group of H, halogen, alkyl, substituted alkyl, aryl, and substituted aryl;

with the proviso that when $R^1$ is

$G^1$, $G^2$, $G^3$ and $G^4$ cannot simultaneously have the following meanings:

$G^1$ and $G^2$=H, $G^3$=O and $G^4$=H or $Z^2C=O$ where $Z^2$=alkyl group.

A preferred compound of Formula II of the invention is Formula IIa

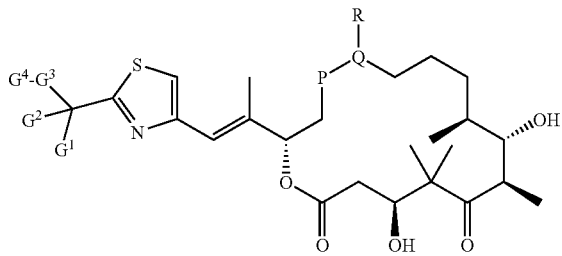

where the symbols have the following meaning:
P-Q is a C,C double bond or an epoxide,
R is a H atom or a methyl group,
G$^1$ is an H atom, an alkyl group, a substituted alkyl group or a halogen atom,
G$^2$ is an H atom, an alkyl group or a substituted alkyl group,
G$^3$ is an O atom, an S atom or an NZ$^1$ group with
Z$^1$ being an H atom, an alkyl group, a substituted alkyl group, an acyl group, or a substituted acyl group, and
G$^4$ is an H atom, an alkyl group, a substituted alkyl group, an OZ$^2$ group, an NZ$^2$Z$^3$ group, a Z$^2$C=O group, a Z$^4$SO$_2$ group or an optionally substituted glycosyl group with Z$^2$ being a H atom, an alkyl group, a substituted alkyl group, an aryl group, a substituted aryl group or a heterocyclic group,
Z$^3$ an H atom, an alkyl group, a substituted alkyl group, an acyl group or a substituted acyl group, and
Z$^4$ an alkyl, a substituted alkyl, an aryl, a substituted aryl or a heterocyclic group, with the proviso that G$^1$, G$^2$, G$^3$ and G$^4$ cannot have simultaneously the following meanings: G$^1$ and G$^2$=H atom, G$^3$=O atom and G$^4$=H atom or Z$^2$C=O with Z$^2$=alkyl group.

A particularly preferred compound of Formula II is [1S-[1R*,3R*(E),7R*,10S*,11R*,12R*,16S*]]-3-[2-[2-(Aminomethyl)-4-thiazolyl]-1-methylethenyl]-7,11-dihydroxy-8,8,10,12,16-pentamethyl-4,17-dioxabicyclo[14.1.0]heptadecane-5,9-dione (Compound 4) and pharmaceutically acceptable salts thereof.

Suitable anti-proliferative agents for use in the methods of the invention, include, without limitation, alkylating agents (including, without limitation, nitrogen mustards, ethylenimine derivatives, alkyl sulfonates, nitrosoureas and triazenes): Uracil mustard, Chlormethine, Cyclophosphamide (Cytoxan@), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide; antimetabolites (including, without limitation, folic acid antagonists, pyrimidine analogs, purine analogs and adenosine deaminase inhibitors), Methotrexate, 5-Fluorouracil, Floxuridine, Cytarabine, 6-Mercaptopurine, 6-Thioguanine, Fludarabine phosphate, Pentostatine, and Gemcitabine; natural products and their derivatives (for example, vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, Ara-C, paclitaxel (paclitaxel is commercially available as Taxol®), Mithramycin, Deoxyco-formycin, Mitomycin-C, L-Asparaginase, Interferons (especially IFN-a), Etoposide, and Teniposide; navelbene, CPT-11, anastrazole, letrazole, capecitabine, reloxafine, cyclophosphamide, ifosamide, and droloxafine and radiation.

The present invention further provides a pharmaceutical composition for the synergistic treatment of cancer which comprises at least one anti-proliferative agent, and a compound of Formulas I and/or II, and a pharmaceutically acceptable carrier.

In a preferred embodiment of the invention the antiproliferative agent is administered simultaneous with or before or after the administration of a compound of Formulas I and/or II.

DETAILED DESCRIPTION OF THE INVENTION

Figure 1:
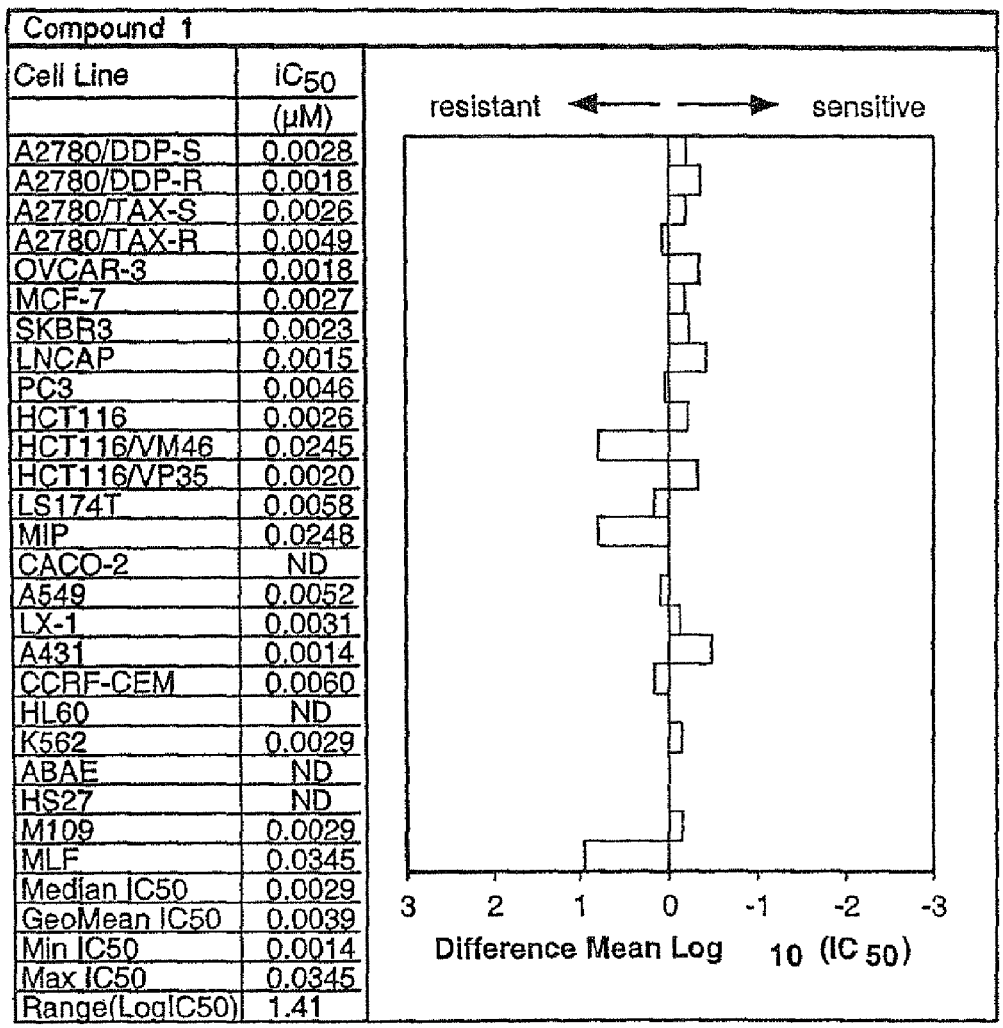
FIG. 1 shows the cytotoxicity spectrum of Compound 1 versus a panel of tumor cell lines in an Oncology Diverse Cell Assay. Bar graphs, on the right, depict the IC$_{50}$ values of the cell lines listed on the left hand column (top to bottom).

In accordance with the present invention, methods for the scheduled administration of epothilone analogs in synergistic combination(s) with at least one additional anti-neoplastic agent for the treatment and prevention of proliferative diseases are provided.

Epothilones mimic the biological effects of taxol, (Bollag et al., Cancer Research 55: 2325-2333 (1995), and in competition studies act as competitive inhibitors of taxol binding to microtubules. However, epothilones enjoy a significant advantage over taxol in that epothilones exhibit a much lower drop in potency compared to taxol against a multiple drug-resistant cell line (Bollag et al. (1995)). Furthermore, epothilones are considerably less efficiently exported from the cells by P-glycoprotein than is taxol (Gerth et al. (1996)).

Thus, in a preferred embodiment, the chemotherapeutic method of the invention comprises the administration of epothilone analog of Formulas I and/or II in combination with other anti-cancer agents. The epothilone analogs disclosed herein, when used in combination with at least one other anti-cancer agent(s) demonstrate superior cytotoxic activity.

A preferred epothilone analog for use in the methods of the invention is a compound of Formula I wherein

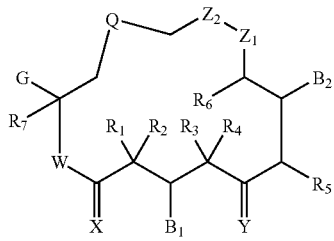

wherein:
Q is selected from the group consisting of

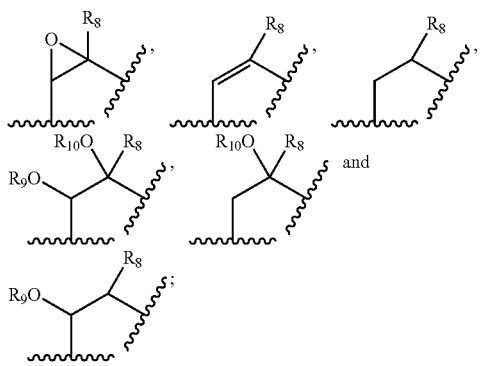

G is selected from the group consisting of alkyl, substituted alkyl, aryl, substituted aryl, heterocyclo,

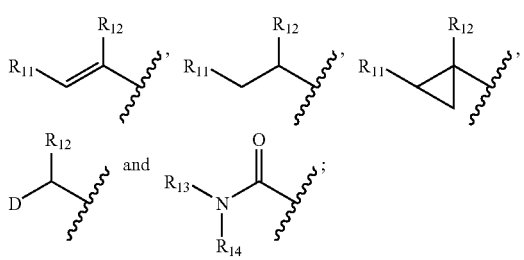

W is O or $NR_{15}$;
X is O or H, H;

Y is selected from the group consisting of O; H, $OR_{16}$; $OR_{17}$, $OR_{17}$; $NOR_{18}$; H, $NHOR_{19}$; H, $NR_2OR_{21}$; H, H; and $CHR_{22}$; wherein $OR_{17}$, $OR_{17}$ can be a cyclic ketal;

$Z_1$ and $Z_2$ are independently selected from the group consisting of $CH_2$, O, $NR_{23}$, S, and $SO_2$, wherein only one of $Z_1$ and $Z_2$ can be a heteroatom;

$B_1$ and $B_2$ are independently selected from the group consisting of $OR_{24}$, $OCOR_{25}$, and O—C(=O)—$NR_{26}R_{27}$, and when $B_1$ is H and Y is OH, H, they can form a six-membered ring ketal or acetal;

D is selected from the group consisting of $NR_{28}R_{29}$, $NR_3OCOR_{31}$ and saturated heterocycle;

$R_1, R_2, R_3, R_4, R_5, R_6, R_7, R_{13}, R_{14}, R_{18}, R_{19}, R_{20}, R_{21}, R_{22}, R_{26}$ and $R_{27}$ are independently selected from the group consisting of H, alkyl, substituted alkyl, and aryl, and when $R_1$ and $R_2$ are alkyl can be joined to form a cycloalkyl, and when $R_3$ and $R_4$ are alkyl can be joined to form a cycloalkyl;

$R_9, R_{10}, R_{16}, R_{17}, R_{24}, R_{25}$ and $R_{31}$ are independently selected from the group consisting of H, alkyl, and substituted alkyl;

$R_8, R_{11}, R_{12}, R_{28}, R_{30}, R_{32}$, and $R_{33}$ are independently selected from the group consisting of H, alkyl, substituted alkyl, aryl, substituted aryl, cycloalkyl and heterocyclo;

$R_{15}, R_{23}$ and $R_{29}$ are independently selected from the group consisting of H, alkyl, substituted alkyl, aryl, substituted aryl, cycloalkyl, heterocyclo, $R_{32}C$=O, $R_{33}SO_2$, hydroxy, O-alkyl or O-substituted alkyl; and pharmaceutically acceptable salts thereof and any hydrates, solvates or geometric, optical and steroisomers thereof;

with the proviso that compounds wherein
W and X are both O; and
$R_1, R_2$ and $R_7$ are H; and
$R_3, R_4$ and $R_6$ are methyl; and
$R_8$ is H or methyl; and
$Z_1$ and $Z_2$ are $CH_2$; and
G is 1-methyl-2-(substituted-4-thiazolyl)ethenyl; and
Q is as defined above
are excluded.

Another preferred epothilone for use in the present invention is a compound of Formula II:

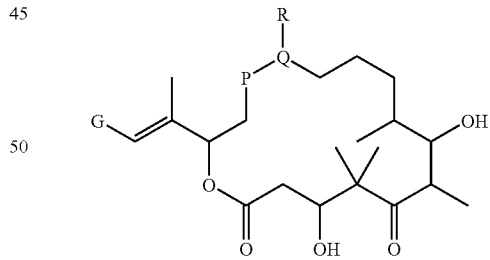

wherein:
P-Q is a C, C double bond or an epoxide;
G is

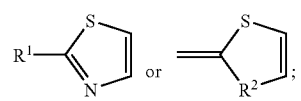

R is selected from the group of H, alkyl, and substituted alkyl;

$R^1$ is selected from the group consisting of

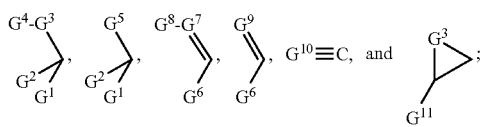

$R^2$ is

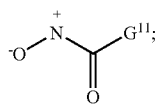

$G^1$ is selected from the group of H, halogen, CN, alkyl and substituted alkyl;

$G^2$ is selected from the group of H, alkyl, and substituted alkyl;

$G^3$ is selected from the group of O, S, and $NZ^1$;

$G^4$ is selected from the group of H, alkyl, substituted alkyl, $OZ^2$, $NZ^2Z^3$, $Z^2C=O$, $Z^4SO_2$, and optionally substituted glycosyl;

$G^5$ is selected from the group of halogen, $N_3$, NCS, SH, CN, NC, $N(Z^1)_3^+$ and heteroaryl;

$G^6$ is selected from the group of H, alkyl, substituted alkyl, $CF_3$, $OZ^5$, $SZ^5$, and $NZ^5Z^6$;

$G^7$ is $CZ^7$ or N;

$G^8$ is selected from the group of H, halogen, alkyl, substituted alkyl, $OZ^{10}$, $SZ^{10}$, $NZ^{10}Z^{11}$;

$G^9$ is selected from the group of O, S, —NH—NH— and —N=N—;

$G^{10}$ is N or $CZ^{12}$ $G^{11}$ is selected from the group of $H_2N$, substituted $H_2N$, alkyl, substituted alkyl, aryl, and substituted aryl;

$Z^2$, $Z^6$, $Z^9$, and $Z^{11}$ are independently selected from the group H, alkyl, substituted alkyl, acyl, and substituted acyl;

$Z^2$ is selected from the group of H, alkyl, substituted alkyl, aryl, substituted aryl, and heterocycle;

$Z^3$, $Z^5$, $Z^8$, and $Z^{10}$ are independently selected from the group H, alkyl, substituted alkyl, acyl, substituted acyl, aryl, and substituted aryl;

$Z^4$ is selected from the group of alkyl, substituted alkyl, aryl, substituted aryl, and heterocycle;

$Z^7$ is selected from the group of H, halogen, alkyl, substituted alkyl, aryl, substituted aryl, $OZ^8$, $SZ^8$, and $NZ^8Z^9$; and $Z^{12}$ is selected from the group of H, halogen, alkyl, substituted alkyl, aryl, and substituted aryl;

with the proviso that when $R^1$ is

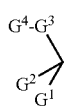

$G^1$, $G^2$, $G^3$ and $G^4$ cannot simultaneously have the following meanings:

$G^1$ and $G^2$=H, $G^3$=O and $G^4$=H or $Z^2C=O$ where $Z^2$=alkyl group.

A preferred compound of Formula II of the invention is Formula IIa:

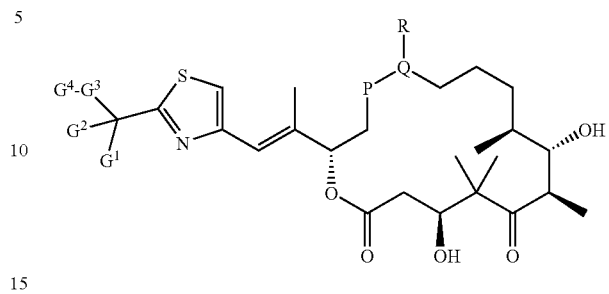

where the symbols have the following meaning:

P-Q is a C,C double bond or an epoxide,

R is a H atom or a methyl group, $G^1$ is an H atom, an alkyl group, a substituted alkyl group or a halogen atom, $G^2$ is an H atom, an alkyl group or a substituted alkyl group, $G^3$ is an O atom, an S atom or an $NZ^1$ group with $Z^1$ being an H atom, an alkyl group, a substituted alkyl group, an acyl group, or a substituted acyl group, and $G^4$ is an H atom, an alkyl group, a substituted alkyl group, an $OZ^2$ group, an $NZ^2Z^3$ group, a $Z^2C=O$ group, a $Z^4SO_2$ group or an optionally substituted glycosyl group with $Z^2$ being a H atom, an alkyl group, a substituted alkyl group, an aryl group, a substituted aryl group or a heterocyclic group, $Z^3$ an H atom, an alkyl group, a substituted alkyl group, an acyl group or a substituted acyl group, and $Z^4$ an alkyl, a substituted alkyl, an aryl, a substituted aryl or a heterocyclic group, with the proviso that $G^1$, $G^2$, $G^3$ and $G^4$ cannot have simultaneously the following meanings: $G^1$ and $G^2$=H atom, $G^3$=O atom and $G^4$=H atom or $Z^2C=O$ with $Z^2$=alkyl group.

A further preferred compound of Formula II is [1S-[1R*,3R*(E),7R*,10S*,11R*,12R*,16S*]]-3-[2-[2-(Aminomethyl)-4-thiazolyl]-1-methylethenyl]-7,11-dihydroxy-8,8,10,12,16-pentamethyl-4,17-dioxabicyclo[14.1.0]heptadecane-5,9-dione (Compound 4) and pharmaceutically acceptable salts thereof. This preferred compound (Compound 4) is of formula:

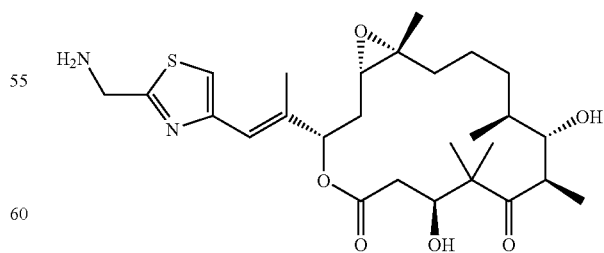

A preferred compound of Formula I is [1S 1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17oxabicyclo[14.1.0]-heptadecane-5,9-dione (Compound 1) and pharmaceutically acceptable salts thereof. This preferred compound (Compound 1) is of formula:

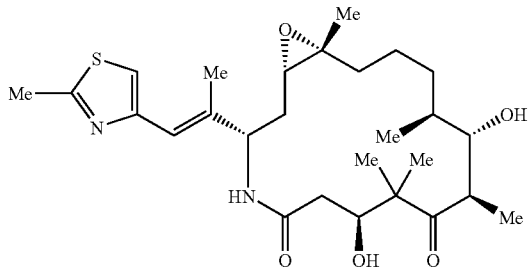 [SMILES: C/C(=C\c1csc(C)n1)[C@@H]1C[C@@H]2O[C@]2(C)CCC[C@H](C)[C@H](O)[C@@H](C)C(=O)C(C)(C)[C@@H](O)CC(=O)N1]

When describing the compounds of the present invention, the phrase "lower alkyl" or "lower alk" (as part of another group) refers to an unsubstituted alkyl group of 1 to 6, preferably 1 to 4, carbon atoms.

The term "aralkyl" refers to an aryl group bonded directly through a lower alkyl group. A preferred aralkyl group is benzyl.

The term "aryl" refers to a monocyclic or bicyclic aromatic hydrocarbon group having 6 to 12 carbon atoms in the ring portion. Exemplary of aryl herein are phenyl, naphthyl and biphenyl groups.

The term "heterocyclo" refers to a fully saturated or unsaturated, aromatic or nonaromatic cyclic group which is a 4 to 7 membered monocyclic, 7 to 11 membered bicyclic, or 10 to 15 membered tricyclic ring system which has at least one heteroatom in at least one carbon atom-containing ring. Each ring of the heterocyclic group containing a heteroatom may have 1, 2, 3 or 4 heteroatoms selected from nitrogen, oxygen and sulfur where the nitrogen and sulfur heteroatoms may also optionally be oxidized and the nitrogen heteroatoms may also optionally be quaternized. The heterocyclo group may be attached at any heteroatom or carbon atom.

Exemplary monocyclic heterocyclo groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydrothiopyranyl, tetrahydropyranyl, morpholinyl, thiamorpholinyl, thiamorpholinyl sulfoxide, tetrahydrothiopyranylsulfone, thiamorpholinyl sulfone, 1,3-dioxolane, tetrahydro-1,1-dioxothienyl, dioxanyl, isothiazolidinyl, thietanyl, thiiranyl, triazinyl, triazolyl, and the like.

Exemplary bicyclic heterocyclo groups include benzothiazolyl, benzoxazolyl, benzothienyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

When a group is referred to as being optionally substituted, it may be substituted with one to five, preferably one to three, substituents such as F, Cl, Br, I, trifluoromethyl, trifluoromethoxy, hydroxy, lower alkoxy, cycloalkoxy, heterocyclooxy, oxo, lower alkanoyl, aryloxy, lower alkanoyloxy, amino, lower alkylamino, arylamino, aralkylamino, cycloalkylamino, heterocycloamino, disubstituted amines in which the two amino substituents independently are selected from lower alkyl, aryl or aralkyl, lower alkanoylamino, aroylamino, aralkanoylamino, substituted lower alkanoylamino, substituted arylamino, substituted aralkylanoylamino, thiol, lower alkylthio, arylthio, aralkylthio, cycloalkylthio, heterocyclothio, lower alkylthiono, arylthiono, aralkylthiono, lower alkylsulfonyl, arylsulfonyl, aralkylsulfonyl, sulfonamide (e.g., $SO_2NH_2$), substituted sulfonamide, nitro, cyano, carboxy, carbamyl (e.g., $CONH_2$), substituted carbamyl (e.g., CONH-lower alkyl, CONH-aryl, CONH-aralkyl or cases where there are two substituents on the nitrogen independently selected from lower alkyl, aryl or aralkyl), lower alkoxycarbonyl, aryl, substituted aryl, guanidino, and heterocyclos (e.g., indolyl, imidazolyl, furyl, thienyl, thiazolyl, pyrrolidyl, pyridyl, pyrimidyl and the like). Where noted above that the substitutent is further substituted, it will be substituted with F, Cl, Br, I, optionally substituted lower alkyl, hydroxy, optionally substituted lower alkoxy, optionally substituted aryl, or optionally substituted aralkyl.

All stereoisomers of the Formula I and II compounds of the instant invention are contemplated, either in admixture or in pure or substantially pure form. The definition of the formula I compounds embraces all possible stereoisomers and their mixtures. The Formula I and II definitions very particularly embrace the racemic forms and the isolated optical isomers having the specified activity.

A particularly preferred epothilone analog for use in the methods of the invention is Compound 1: [1S-[1R*,3R*(E), 7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione.

Another preferred epothilone is Compound 4: [1S-[1R*,3R* (E),7R*,10S*,11R*,12R*,16S*]]-3-[2-[2-(Aminomethyl)-4-thiazolyl]-1-methylethenyl]-7,11-dihydroxy-8,8,10,12, 16-pentamethyl-4,17-dioxabicyclo[14.1.0]heptadecane-5,9-dione.

Compound 1, an exemplary epothilone analog of the invention, is a semi-synthetic epothilone analog and has a mode of action analogous to paclitaxel (i.e., microtubule stabilization). However, in preclinical pharmacology studies, Compound 1 has demonstrated significant improvement over paclitaxel in several critical aspects. Compound 1 exhibits a very impressive and broad spectrum of antitumor activity against paclitaxel-sensitive (A2780, HCT116 and LS174T) and, more importantly, as well as paclitaxel-resistant human colon tumors (HCT116/VM46), ovarian carcinoma (Pat-7 and A2780Tax) and breast carcinoma (Pat-21) models. Compound 1 is orally efficacious; the antitumor activity produced after oral administration is comparable to that produced by parenteral administration of the drug. These preclinical efficacy data indicate that Compound 1 demonstrates improved clinical efficacy in TAXOL®-insensitive and sensitive disease types.

In a preferred embodiment of the invention a compound of Formulas I and/or II is administered in conjunction with at least one anti-neoplastic agent.

As used herein, the phrase "anti-neoplastic agent" is synonymous with "chemotherapeutic agent" and/or "anti-proliferative agent" and refers to compounds that prevent cancer, or hyperproliferative cells from multiplying. Anti-proliferative agents prevent cancer cells from multiplying by: (1) interfering with the cell's ability to replicate DNA and (2) inducing cell death and/or apoptosis in the cancer cells.

Classes of compounds that may be used as anti-proliferative cytotoxic agents include the following:

Alkylating agents (including, without limitation, nitrogen mustards, ethylenimine derivatives, alkyl sulfonates, nitrosoureas and triazenes): Uracil mustard, Chlormethine, Cyclophosphamide (Cytoxan@), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide.

Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (for example, vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, Ara-C, paclitaxel (paclitaxel is commercially available as Taxol®), Mithramycin, Deoxyco-formycin, Mitomycin-C, L-Asparaginase, Interferons (especially IFN-a), Etoposide, and Teniposide.

Other anti-proliferative cytotoxic agents are navelbene, CPT-11, anastrazole, letrazole, capecitabine, reloxafine, cyclophosphamide, ifosamide, and droloxafine.

The phrase "radiation therapy" includes, but is not limited to, x-rays or gamma rays which are delivered from either an externally applied source such as a beam or by implantation of small radioactive sources Microtubule affecting agents interfere with cellular mitosis and are well known in the art for their anti-proliferative cytotoxic activity. Microtubule affecting agents useful in the invention include, but are not limited to, allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl) ethenyl]-4-aza-17 oxabicyclo[14.1.0]heptadecane-5,9-dione (disclosed in U.S. Pat. No. 6,262,094, issued Jul. 17, 2001), [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo [14.1.0]-heptadecane-5,9-dione (disclosed in U.S. Ser. No. 09/506,481 filed on Feb. 17, 2000, and examples 7 and 8 herein), and derivatives thereof; and other microtubule-disrupter agents. Additional antineoplastic agents include, discodermolide (see Service, (1996) Science, 274:2009) estramustine, nocodazole, MAP4, and the like. Examples of such agents are also described in the scientific and patent literature, see, e.g., Bulinski (1997) *J. Cell Sci.* 110:3055 3064; Panda (1997) *Proc. Natl. Acad. Sci. USA* 94:10560-10564; Muhlradt (1997) Cancer Res. 57:3344-3346; Nicolaou (1997) *Nature* 387:268-272; Vasquez (1997) *Mol. Biol. Cell.* 8:973-985; Panda (1996) *J. Biol. Chem.* 271:29807-29812.

In cases where it is desirable to render aberrantly proliferative cells quiescent in conjunction with or prior to treatment with the chemotherapeutic methods of the invention, hormones and steroids (including synthetic analogs): 17a-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, chlorotrianisene, Hydroxyprogesterone, Aminoglutethimide, Estramustine, Medroxyprogesteroneacetate, Leuprolide, Flutamide, Toremifene, Zoladex can also be administered to the patient.

Also suitable for use in the combination chemotherapeutic methods of the invention are antiangiogenics such as matrix metalloproteinase inhibitors, and other VEGF inhibitors, such as anti-VEGF antibodies and small molecules such as ZD6474 and SU6668 are also included. Anti-Her2 antibodies from Genetech may also be utilized. A suitable EGFR inhibitor is EKB-569 (an irreversible inhibitor). Also included are Imclone antibody C225 immunospecific for the EGFR, and src inhibitors.

Also suitable for use as an antiproliferative cytostatic agent is Casodex™ which renders androgen-dependent carcinomas non-proliferative. Yet another example of a cytostatic agent is the antiestrogen Tamoxifen which inhibits the proliferation or growth of estrogen dependent breast cancer. Inhibitors of the transduction of cellular proliferative signals are cytostatic agents. Examples are epidermal growth factor inhibitors, Her-2 inhibitors, MEK-1 kinase inhibitors, MAPK kinase inhibitors, PI3 inhibitors, Src kinase inhibitors, and PDGF inhibitors.

As mentioned, certain anti-proliferative agents are anti-angiogenic and antivascular agents and, by interrupting blood flow to solid tumors, render cancer cells quiescent by depriving them of nutrition. Castration, which also renders androgen dependent carcinomas non-proliferative, may also be utilized. Starvation by means other than surgical disruption of blood flow is another example of a cytostatic agent. A particularly preferred class of antivascular cytostatic agents is the combretastatins. Other exemplary cytostatic agents include MET kinase inhibitors, MAP kinase inhibitors, inhibitors of non-receptor and receptor tyrosine kinases, inhibitors of integrin signaling, and inhibitors of insulin-like growth factor receptors.

Thus, the present invention provides methods for the synergistic treatment of a variety of cancers, including, but not limited to, the following:

carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma);

hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma;

hematopoietic tumors of myeloid lineage including acute and chronic myelogenous leukemias, myelodysplastic syndrome, myeloid leukemia, and promyelocytic leukemia;

tumors of the central and peripheral nervous system including astrocytoma, neuroblastoma, glioma, and schwannomas;

tumors of mesenchymal origin including fibrosarcoma, rhabdomyoscarcoma, and osteosarcoma; and other tumors including melanoma, xenoderma pigmentosum, keratoactanthoma, seminoma, thyroid follicular cancer, and teratocarcinoma.

Most preferably, the invention is used to treat accelerated or metastatic cancers of the bladder, pancreatic cancer, prostate cancer, non-small cell lung cancer, colorectal cancer, and breast cancer.

In a preferred embodiment of this invention, a method is provided for the synergistic treatment of cancerous tumors. Advantageously, the synergistic method of this invention reduces the development of tumors, reduces tumor burden, or produces tumor regression in a mammalian host.

Methods for the safe and effective administration of most of these chemotherapeutic agents are known to those skilled in the art. In addition, their administration is described in the standard literature.

For example, the administration of many of the chemotherapeutic agents is described in the "Physicians' Desk Reference" (PDR), e.g., 1996 edition (Medical Economics Company, Montvale, N.J. 07645-1742, USA); the disclosure of which is incorporated herein by reference thereto.

Preferred compounds of Formula I for use in the methods of the present invention include: [1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4,13,17-trioxabicyclo[14.1.0]heptadecane-5,9-dione; [1S-[1R*,3R*(E),7R*,10S*,11R*,12R*,16S*]]-7,11-dihydroxy-8,8,10,12-tetramethyl-3-[1-methyl-2-(2-methyl-4-thiazolyl)ethenyl]-4,13,17-trioxabicyclo[14.1.0]heptadecane-5,9-dione; [4S-[4R*,7S*,8R*,9R*,15R*(E)]]-4,8-dihydroxy-5,5,7,9,13-pentamethyl-16-[1-methyl-2-(2-methyl-4-thiazolyl)ethenyl]-1,10-dioxa-13-cyclohexadecene-2,6-dione; [4S-[4R*,7S*,8R*,9R*,15R*(E)]]-4,8-dihydroxy-5,5,7,9-tetramethyl-16-[1-methyl-2-(2-methyl-4-thiazolyl)ethenyl]-1,10-dioxa-13-cyclohexadecene-2,6-dione; [1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4,14,17-trioxabicyclo[14.1.0]heptadecane-5,9-dione; [1S-[1R*,3R*(E), 7R*,10S*,11R*,12R*,16S*]]-7,11-dihydroxy-8,8,10,12-tetramethyl-3-[1-methyl-2-(2-methyl-4-thiazolyl)ethenyl]-4,14,17-trioxabicyclo[14.1.0]heptadecane-5,9-dione; [4S-[4R*,7S*,8R*,9R*,15R*(E)]]-4,8-dihydroxy-5,5,7,9,13-pentamethyl-16-[1-methyl-2-(2-methyl-4-thizolyl)ethenyl]-1,1'-dioxa-13-cyclohexadecene-2,6-dione; [4S-[4R*,7S*,8R*,9R*,15R*(E)]]-4,8-dihydroxy-5,5,7,9-tetramethyl-16-[1-methyl-2-(2-methyl-4-thizolyl)ethenyl]-1,1'-dioxa-13-cyclohexadecene-2,6-dione; [1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4,17-dioxabicyclo[14.1.0]heptadecane-9-one; [1S-[1R*,3R*(E),7R*,10S*,11R*,12R*,16S*]]-7,11-dihydroxy-8,8,10,12-tetramethyl-3-[1-methyl-2-(2-methyl-4-thiazolyl)ethenyl]-4,17-dioxabicyclo[14.1.0]heptadecane-9-one; [1S-[1R*,3R*(E),7R*,10S*,11R*,12R*,16S*]]-7,11-dihydroxy-3,8,8,10,12,16-hexamethyl-3-[1-methyl-2-(2-methyl-4-thiazolyl)ethenyl]-4,17-dioxabicyclo[14.1.0]heptadecane-5,9-dione; [1S-[1R*,3R*(E), 7R*,10S*,11R*,12R*,16S*]]-7,11-dihydroxy-3,8,8,10,12-pentamethyl-3-[1-methyl-2-(2-methyl-4-thiazolyl)ethenyl]-4,17-dioxabicyclo[14.1.0]heptadecane-5,9-dione; [4S-[4R*,7S*,8R*,9R*,15R*(E)]]-4,8-dihydroxy-5,5,7,9,13,16-hexamethyl-16-[1-methyl-2-(2-methyl-4-thiazolyl)ethenyl]-1-oxa-13-cyclohexadecene-2,6-dione; [4S-[4R*,7S*,8R*,9R*,15R*(E)]]-4,8-dihydroxy-5,5,7,9,16-pentamethyl-16-[1-methyl-2-(2-methyl-4-thiazolyl)ethenyl]-1-oxa-13-cyclohexadecene-2,6-dione; [1S-[1R*,3R*(E), 7R*,10S*,11R*,12R*,16S*]]-7,11-dihydroxy-8,8,10,12,16-pentamethyl-3-[1-methyl-2-(2-methyl-4-thiazolyl)ethenyl]-4,17-dioxabicyclo[14.1.0]heptadecane-5,9-dione; [1S-[1R*,3R*(E), 7R*,10S*,11R*,12R*,16S*]]-7,11-dihydroxy-6,8,8,10,12-pentamethyl-3-[1-methyl-2-(2-methyl-4-thiazolyl)ethenyl]-4,17-dioxabicyclo[14.1.0]heptadecane-5,9-dione; [1S-[1R*,3R*(E), 7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione; [1S-[1R*,3R*(E), 7R*,10S*,11R*,12R*,16S*]]-7,11-dihydroxy-8,8,10,12-tetramethyl-3-[1-methyl-2-(2-methyl-4-thiazolyl)ethenyl]-4-aza-17-oxabicyclo[14.1.0]heptadecane-5,9-dione; [4S-[4R*,7S*,8R*,9R*,15R*(E)]]-4,8-dihydroxy-5,5,7,9,13-pentamethyl-16-[1-methyl-2-(2-methyl-4-thiazolyl)ethenyl]-1-aza-13-cyclohexadecene-2,6-dione; [4S-[4R*,7S*,8R*,9R*,15R*(E)]]-4,8-dihydroxy-5,5,7,9-tetramethyl-16-[1-methyl-2-(2-methyl-4-thiazolyl)ethenyl]-1-aza-13-cyclohexadecene-2,6-dione; [1S-[1R*,3R*(E), 7R*,10S*,11R*,12R*,16S*]]-7,11-dihydroxy-4,8,8,10,12,16-hexamethyl-3-[1-methyl-2-(2-methyl-4-thiazolyl)ethenyl]-4-aza-17-oxabicyclo[14.1.0]heptadecane-5,9-dione; [1S-[1R*,3R*(E), 7R*,10S*,11R*,12R*,16S*]]-7,11-dihydroxy-4,8,8,10,12-pentamethyl-3-[1-methyl-2-(2-methyl-4-thiazolyl)ethenyl]-4-aza-17-oxabicyclo[14.1.0]heptadecane-5,9-dione; [4S-[4R*,7S*,8R*,9R*,15R*(E)]]-4,8-dihydroxy-1,5,5,7,9,13-hexamethyl-16-[1-methyl-2-(2-methyl-4-thiazolyl)ethenyl]-1-aza-13-cyclohexadecene-2,6-dione; [4S-[4R*,7S*,8R*,9R*,15R*(E)]]-4,8-dihydroxy-1,5,5,7,9-pentamethyl-16-[1-methyl-2-(2-methyl-4-thiazolyl)ethenyl]-1-aza-13-cyclohexadecene-2,6-dione; [1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-13-aza-4,17-dioxabicyclo[14.1.0]heptadecane-5,9-dione; [1S-[1R*,3R*(E),7R*,10S*,11R*,12R*,16S*]]-7,11-dihydroxy-8,8,10,12-tetramethyl-3-[1-methyl-2-(2-methyl-4-thiazolyl)ethenyl]-13-aza-4,17-dioxabicyclo[14.1.0]heptadecane-5,9-dione; [4S-[4R*,7S*,8R*,9R*,15R*(E)]]-4,8-dihydroxy-5,5,7,9,13-pentamethyl-16-[1-methyl-2-(2-methyl-4-thiazolyl)ethenyl]-10-aza-1-oxa-13-cyclohexadecene-2,6-dione; [4S-[4R*,7S*,8R*,9R*,15R*(E)]]-4,8-dihydroxy-5,5,7,9-tetramethyl-16-[1-methyl-2-(2-methyl-4-thiazolyl)ethenyl]-10-aza-1-oxa-13-cyclohexadecene-2,6-dione; [1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-14-aza-4,17-dioxabicyclo[14.1.0]heptadecane-5,9-dione; [1S-[1R*,3R*(E),7R*,10S*,11R*,12R*,16S*]]-7,11-dihydroxy-8,8,10,12-tetramethyl-3-[1-methyl-2-(2-methyl-4-thiazolyl)ethenyl]-14-aza-4,17-dioxabicyclo[14.1.0]heptadecane-5,9-dione; [4S-[4R*,7S*,8R*,9R*,15R*(E)]]-4,8-dihydroxy-5,5,7,9,13-pentamethyl-16-[1-methyl-2-(2-methyl-4-thiazolyl)ethenyl]-11-aza-1-oxa-13-cyclohexadecene-2,6-dione; [4S-[4R*,7S*,8R*,9R*,15R*(E)]]-4,8-dihydroxy-5,5,7,9-tetramethyl-16-[1-methyl-2-(2-methyl-4-thiazolyl)ethenyl]-11-aza-1-oxa-13-cyclohexadecene-2,6-dione; [1S-[1R*,3R*,7R*,10S*,11R*,12R*,16S*]]-N-phenyl-7,11-dihydroxy-8,8,10,12,16-pentamethyl-5,9-dioxo-4,17-dioxabicyclo[14.1.0]heptadecane-3-carboxamide; [1S-[1R*,3R*,7R*,10S*,11R*,12R*,16S*]]-N-phenyl-7,11-dihydroxy-8,8,10,12-tetramethyl-5,9-dioxo-4,17-dioxabicyclo[14.1.0]

heptadecane-3-carboxamide; [4S-[4R*,7S*,8R*,9R*, 15R*]]-N-phenyl-4,8-dihydroxy-5,5,7,9,13-pentamethyl-2, 6-dioxo-1-oxa-13-cyclohexadecene-16-carboxamide; [4S-[4R*,7S*,8R*,9R*,15R*]]-N-phenyl-4,8-dihydroxy-5,5,7, 9-tetramethyl-2,6-dioxo-1-oxa-13-cyclohexadecene-16-carboxamide; [1S[1R*,3R*(E),7R*,10S*,11R*,12R*, 16S*]]-7,11-dihydroxy-8,8,10,12,16-pentamethyl-3-[1-methyl-2-(2-methyl-4-thiazolyl)cyclopropyl]-4,17-dioxabicyclo[14.1.0]heptadecane-5,9-dione; [1S-[1R*,3R* (E),7R*,10S*,11R*,12R*,16S*]]-7,11-dihydroxy-8,8,10, 12-tetramethyl-3-[1-methyl-2-(2-methyl-4-thiazolyl) cyclopropyl]-4,17-dioxabicyclo[14.1.0]heptadecane-5,9-dione; and [4S-[4R*,7S*,8R*,9R*,15R*(E)]]-4,8-dihydroxy-5,5,7,9,13-pentamethyl-16-[1-methyl-2-(2-hydroxymethyl-4-thiazolyl)ethenyl]-1-aza-13(Z)-cyclohexadecene-2,6-dione; and pharmaceutically acceptable salts, solvates and hydrates thereof.

Preferred compounds of Formula II for use in the methods of the invention include:

[1S-[1R*,3R*(E),7R*,10S*,11R*,12R*,16S*]]-3-[2-[2-(Azidomethyl)-4-thiazolyl]-1-methylethenyl]-7,11-dihydroxy-8,8,10,12,16-pentamethyl-4,17-dioxabicyclo [14.1.0]heptadecane-5,9-dione;

[1S-[1R*,3R*(E),7R*,10S*,11R*,12R*,16S*]]-3-[2-[2-(Aminomethyl)-4-thiazolyl]-1-methylethenyl]-7,11-dihydroxy-8,8,10,12,16-pentamethyl-4,17-dioxabicyclo [14.1.0]heptadecane-5,9-dione;

[1S-[1R*,3R*(E),7R*,10S*,11R*,12R*,16S*]]-3-[2-[2-[[[(1,1-Dimethylethoxy)carbonyl]amino]methyl]-4-thiazolyl]-1-methylethenyl]-7,11-dihydroxy-8,8,10,12,16-pentamethyl-4,17-dioxabicyclo[14.1.0]heptadecane-5,9-dione;

[4S-[4R*,7S*,8R*,9R*,15R*(E)]]-16-[2-[2-[[[(1,1-Dimethylethoxy)carbonyl]amino]methyl]-4-thiazolyl]-1-methylethenyl]-4,8-dihydroxy-5,5,7,9,13-pentamethyl-1-oxa-13 (Z)-cyclohexadecene-2,6-dione;

[4S-[4R*,7S*,8R*,9R*,15R*(E)]]-16-[2-[2-(Aminomethyl)-4-thiazolyl]-1-methylethenyl]-4,8-dihydroxy-5,5, 7,9,13-pentamethyl-1-oxa-13(Z)-cyclohexadecene-2,6-dione;

[1S-[1R*,3R*(E),7R*,10S*,11R*,12R*,16S*]]-7,11-Dihydroxy-8,8,10,12-tetramethyl-3-[1-methyl-2-[2-[(pentanoyloxy)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-[2-[(naphthoyloxy)methyl]-4-thiazolyl]ethenyl]-4,17-dioxabicyclo [14.1.0]heptadecane-5,9-dione;

[1S-[1R*,3R*(E),7R*,10S*,11R*,12R*,16S*]]-7,11-Dihydroxy-3-[2-[2-[[(2-methoxyethoxy)acetyloxy]methyl]-1-methyl-4-thiazolyl]ethenyl]-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-[2-[(N-propionylamino)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-3-[2-(3-Acetyl-2,3-dihydro-2-methylene-4-thiazolyl)-1-methylethenyl]-7,11-dihydroxy-8,8,10,12-tetramethyl-4,17-dioxabicyclo[14.1.0]heptadecane-5,9-dione, N-oxide;

[1S-[1R*,3R*(E),7R*,10S*,11R*,12R*,16S*]]-7,11-Dihydroxy-3-[2-[2-(methoxymethyl)-4-thiazolyl]-1-methylethenyl]-8,8,10,12-tetramethyl-4,17-dioxabicyclo[14.1.0] heptadecane-5,9-dione;

[1S-[1R*,3R*(E),7R*,10S*,11R*,12R*,16S*]]-7,11-Dihydroxy-8,8,10,12,16-pentamethyl-3-[1-methyl-2-(phenoxymethyl)-4-thiazolyl]ethenyl]-4,17-dioxabicyclo [14.1.0]heptadecane-5,9-dione;

[1S-[1R*,3R*(E),7R*,10S*,11R*,12R*,16S*]]-3-[2-[2-[(Ethylthio)methyl]-4-thiazolyl]-1-methylethenyl]-7,11-dihydroxy-8,8,10,12,16-pentamethyl-4,17-dioxabicyclo [14.1.0]heptadecane-5,9-dione;

[1S-[1R*,3R*(E),7R*,10S*,11R*,12R*,16S*]]-3-[2-[2-(Ethoxymethyl)-4-thiazolyl]-1-methylethenyl]-7,11-dihydroxy-8,8,10,12-tetramethyl-4,17-dioxabicyclo [14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-[2-[(2,3,4,6-tetraacetyl-alpha-glucosyloxy)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-[2-[(2',3',4', 6'-tetraacetyl-beta-glucosyloxy)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-[2-[(6'-acetyl-alpha-glucosyloxy)methyl]-4-thiazolyl]ethenyl]-4, 17-dioxabicyclo[14.1.0]heptadecane-5,9-dione;

[1S-[1R*,3R*(E),7R*,10S*,11R*,12R*,16S*]]-7,11-Dihydroxy-8,8,10,12,16-pentamethyl-3-[1-methyl-2-[2-[(p-toluenesulfonyloxy)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-3-[2-[2-(Bromomethyl)-4-thiazolyl]-1-methylethenyl]-7,11-dihydroxy-8,8,10,12-tetramethyl-4,17-dioxabicyclo[14.1.0] heptadecane-5,9-dione;

[1S-[1R*,3R*(E),7R*,10S*,11R*,12R*,16S*]]-3-[2-(5-Bromo-2-methyl-4-thiazolyl)-1-methylethenyl]-7,11-dihydroxy-8,8,10,12-tetramethyl-4,17-dioxabicyclo [14.1.0]heptadecane-5,9-dione;

[1S-[1R*,3R*(E),7R*,10S*,11R*,12R*,16S*]]-3-[2-[2-(Cyanomethyl)-4-thiazolyl]-1-methylethenyl]-7,11-dihydroxy-8,8,10,12,16-pentamethyl-4,17-dioxabicyclo [14.1.0]heptadecane-5,9-dione;

[4S-[4R*,7S*,8R*,9R*,15R*(E)]]-16-[2-[2-(Cyanomethyl)-4-thiazolyl]-1-methylethenyl]-4,8-dihydroxy-5,5, 7,9,13-pentamethyl-1-oxa-13(Z)-cyclohexadecene-2,6-dione;

[1S-[1R*,3R*(E),7R*,10S*,11R*,12R*,16S*]]-7,11-Dihydroxy-3-[2-[2-(1H-imidazol-1-ylmethyl)-4-thiazolyl]-1-methylethenyl]-8,8,10,12,16-pentamethyl-4,17-dioxabicyclo[14.1.0]heptadecane-5,9-dione;

[1S-[1R*,3R*(E),7R*,10S*,11R*,12R*,16S*]]-3-[2-(2-Formyl-4-thiazolyl)-1-methylethenyl]-7,11-dihydroxy-8, 8,10,12-tetramethyl-4,17-dioxabicyclo[14.1.0]heptadecane-5,9-dione;

[1S-[1R*,3R*(E),7R*,10S*,11R*,12R*,16S*]]-3-[2-(2-Formyl-4-thiazolyl)-1-methylethenyl]-7,11-dihydroxy-8, 8,10,12,16-pentamethyl-4,17-dioxabicyclo[14.1.0]heptadecane-5,9-dione;

[1S-[1R*,3R*(E),7R*,10S*,11R*,12R*,16S*]]-3-[2-(2-Ethenyl-4-thiazolyl)-1-methylethenyl]-7,11-dihydroxy-8, 8,10,12-tetramethyl-4,17-dioxabicyclo[14.1.0]heptadecane-5,9-dione;

[1S-[1R*,3R*(E),7R*,10S*,11R*,12R*,16S*]]-7,11-Dihydroxy-3-[2-[2-(methoxyimino)-4-thiazolyl]-1-methylethenyl]-8,8,10,12-tetramethyl-4,17-dioxabicyclo[14.1.0] heptadecane-5,9-dione;

[1S-[1R*,3R*(E),7R*,10S*,11R*,12R*,16S*]]-7,11-Dihydroxy-8,8,10,12-tetramethyl-3-[1-methyl-2-[2-[[(phenylmethyl)imino]methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-3-[2-(2-Acetyl-4-thiazolyl)-1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-(2-oxiranyl-4-thiazolyl)ethenyl]-4,17-dioxabicyclo[14.1.0]heptadecane-5,9-dione;

[1S-[1R*,3R*(E),7R*,10S*,11R*,12R*,16S*]]-7,11-Dihydroxy-3-[2-[2-(2-iodoethenyl)-4-thiazolyl]-1-methylethenyl]-8,8,10,12-tetramethyl-4,17-dioxabicyclo[14.1.0]heptadecane-5,9-dione;

[1S-[1R*,3R*(E),7R*,10S*,11R*,12R*,16S*]]-3-[2-(2-Ethynyl-4-thiazolyl)-1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-Dihydroxy-8,8,10,12,16-pentamethyl-3-[1-methyl-2-[2-[(methylamino)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-3-[2-[2-[[[2-(Dimethylamino)ethyl]amino]methyl]-4-thiazolyl]-1-methylethenyl]-7,11-dihydroxy-8,8,10,12,16-pentamethyl-4,17-dioxabicyclo[14.1.0]heptadecane-5,9-dione;

[1S-[1R*,3R*(E),7R*,10S*,11R*,12R*,16S*]]-3-[2-[2-[(Dimethylamino)methyl]-4-thiazolyl]-1-methylethenyl]-7,11-dihydroxy-8,8,10,12,16-pentamethyl-4,17-dioxabicyclo[14.1.0]heptadecane-5,9-dione;

[1S-[1R*,3R*(E),7R*,10S*,11R*,12R*,16S*]]-3-[2-[2-[[Bis(2-methoxyethyl)amino]methyl]-4-thiazolyl]-1-methylethenyl]-7,11-dihydroxy-8,8,10,12,16-pentamethyl-4,17-dioxabicyclo[14.1.0]heptadecane-5,9-dione;

[1S-[1R*,3R*(E),7R*,10S*,11R*,12R*,16S*]]-7,11-Dihydroxy-8,8,10,12,16-pentamethyl-3-[1-methyl-2-[2-[(4-methyl-1-piperazinyl)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-4-[2-(7,11-Dihydroxy-8,8,10,12-tetramethyl-5,9-dioxo-4,17-dioxabicyclo[14.1.0]heptadecan-3-yl)-1-propenyl]-2-thiazolecarboxylic acid;

[1S-[1R*,3R*(E),7R*,10S*,11R*,12R*,16S*]]-4-[2-(7,11-Dihydroxy-8,8,10,12-tetramethyl-5,9-dioxo-4,17-dioxabicyclo[14.1.0]heptadecan-3-yl)-1-propenyl]-2-thiazolecarboxylic acid methyl ester and the pharmaceutically acceptable salts, solvents and hydrates thereof.

The Formula I compounds may be prepared by the procedures described in WO/9902514. The Formula II compounds may be prepared by the procedures described in U.S. Pat. No. 6,262,094.

The compounds of Formulas I and II are useful in various pharmaceutically acceptable salt forms. The term "pharmaceutically acceptable salt" refers to those salt forms which would be apparent to the pharmaceutical chemist, i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flowability of the resulting bulk drug. Conveniently, pharmaceutical compositions may be prepared from the active ingredients or their pharmaceutically acceptable salts in combination with pharmaceutically acceptable carriers.

Pharmaceutically acceptable salts of the Formula I and II compounds which are suitable for use in the methods and compositions of the present invention include, but are not limited to, salts formed with a variety of organic and inorganic acids such as hydrogen chloride, hydroxymethane sulfonic acid, hydrogen bromide, methanesulfonic acid, sulfuric acid, acetic acid, trifluoroacetic acid, maleic acid, benzenesulfonic acid, toluenesulfonic acid, sulfamic acid, glycolic acid, stearic acid, lactic acid, malic acid, pamoic acid, sulfanilic acid, 2-acetoxybenzoic acid, fumaric acid, toluenesulfonic acid, methanesulfonic acid, ethanedisulfonic acid, oxalic acid, isethonic acid, and include various other pharmaceutically acceptable salts, such as, e.g., nitrates, phosphates, borates, tartrates, citrates, succinates, benzoates, ascorbates, salicylates, and the like. Cations such as quaternary ammonium ions are contemplated as pharmaceutically acceptable counterions for anionic moieties.

Preferred salts of Formula I and II compounds include hydrochloride salts, methanesulfonic acid salts and trifluoroacetic acid salts. In addition, pharmaceutically acceptable salts of the Formula I and/or II compounds may be formed with alkali metals such as sodium, potassium and lithium; alkaline earth metals such as calcium and magnesium; organic bases such as dicyclohexylamine, tributylamine, and pyridine; and amino acids such as arginine, lysine and the like.

The pharmaceutically acceptable salts of the present invention can be synthesized by conventional chemical methods. Generally, the salts are prepared by reacting the free base or acid with stoichiometric amounts or with an excess of the desired salt-forming inorganic or organic acid or base, in a suitable solvent or solvent combination.

The present invention also encompasses a pharmaceutical composition useful in the treatment of cancer, comprising the administration of a therapeutically effective amount of the combinations of this invention, with or without pharmaceutically acceptable carriers or diluents. The synergistic pharmaceutical compositions of this invention comprise an antiproliferative agent or agents, a formula I compound, and a pharmaceutically acceptable carrier. The methods entail the use of a neoplastic agent in combination with a Formula I and/or Formula II compound. The compositions of the present invention may further comprise one or more pharmaceutically acceptable additional ingredient(s) such as alum, stabilizers, antimicrobial agents, buffers, coloring agents, flavoring agents, adjuvants, and the like. The antineoplastic agents, Formula I, Formula II compounds and compositions of the present invention may be administered orally or parenterally including the intravenous, intramuscular, intraperitoneal, subcutaneous, rectal and topical routes of administration.

For oral use, the antineoplastic agents, Formula I and/or Formula II compounds and compositions of this invention may be administered, for example, in the form of tablets or capsules, powders, dispersible granules, or cachets, or as aqueous solutions or suspensions. In the case of tablets for oral use, carriers which are commonly used include lactose, corn starch, magnesium carbonate, talc, and sugar, and lubricating agents such as magnesium stearate are commonly added. For oral administration in capsule form, useful carriers include lactose, corn starch, magnesium carbonate, talc, and sugar. When aqueous suspensions are used for oral administration, emulsifying and/or suspending agents are commonly added.

In addition, sweetening and/or flavoring agents may be added to the oral compositions. For intramuscular, intraperitoneal, subcutaneous and intravenous use, sterile solutions of the active ingredient(s) are usually employed, and the pH of the solutions should be suitably adjusted and buffered. For intravenous use, the total concentration of the solute(s) should be controlled in order to render the preparation isotonic.

For preparing suppositories according to the invention, a low melting wax such as a mixture of fatty acid glycerides or cocoa butter is first melted, and the active ingredient is dispersed homogeneously in the wax, for example by stirring. The molten homogeneous mixture is then poured into conveniently sized molds and allowed to cool and thereby solidify.

Liquid preparations include solutions, suspensions and emulsions. Such preparations are exemplified by water or water/propylene glycol solutions for parenteral injection. Liquid preparations may also include solutions for intranasal administration.

Aerosol preparations suitable for inhalation may include solutions and solids in powder form, which may be in combination with a pharmaceutically acceptable carrier, such as an inert compressed gas.

Also included are solid preparations which are intended for conversion, shortly before use, to liquid preparations for either oral or parenteral administration. Such liquid forms include solutions, suspensions and emulsions.

The compounds of Formula I and II, as well as the anti-neoplastic agents, described herein may also be delivered transdermally. The transdermal compositions can take the form of creams, lotions, aerosols and/or emulsions and can be included in a transdermal patch of the matrix or reservoir type as are conventional in the art for this purpose.

The combinations of the present invention may also be used in conjunction with other well known therapies that are selected for their particular usefulness against the condition that is being treated.

If formulated as a fixed dose, the active ingredients of the combination compositions of this invention are employed within the dosage ranges described below. Alternatively, the anti-neoplastic, and Formula I and Formula II compounds may be administered separately in the dosage ranges described below. In a preferred embodiment of the present invention, the antineoplastic agent is administered in the dosage range described below following or simultaneously with administration of the Formula I compound in the dosage range described below.

Table I sets forth preferred chemotherapeutic combinations and exemplary dosages for use in the methods of the present invention. Where "Compound of Formula I" appears, any of the variations of Formula I or Formula II set forth herein are contemplated for use in the chemotherapeutic combinations. Preferably, Compound 1 or Compound 4 is employed.

TABLE 1

| CHEMOTHERAPEUTIC COMBINATION | DOSAGE mg/m² (per dose) |
|---|---|
| Compound of Formula I + | 0.1-100 mg/m2 |
| Cisplatin | 5-150 mg/m2 |
| Compound of Formula I + | 0.1-100 mg/m2 |
| Carboplatin | 5-1000 mg/m2 |
| Compound of Formula I + | 0.1-100 mg/m2 |
| Radiation | 200-8000 cGy |
| Compound of Formula I + | 0.1-100 mg/m2 |
| CPT-11 | 5-400 mg/m2 |
| Compound of Formula I + | 0.1-100 mg/m2 |
| Paclitaxel | 40-250 mg/m2 |
| Compound of Formula I + | 0.1-100 mg/m2 |
| Paclitaxel + | 40-250 mg/m2 |
| Carboplatin | 5-1000 mg/m2 |

TABLE 1-continued

| CHEMOTHERAPEUTIC COMBINATION | DOSAGE mg/m² (per dose) |
|---|---|
| Compound of Formula I + | 0.1-100 mg/m2 |
| 5FU and optionally + | 5-5000 mg/m2 |
| Leucovorin | 5-1000 mg/m2 |
| Compound of Formula I + | 0.1-100 mg/m2 |
| Epothilone | 1-500 mg/m2 |
| Compound of Formula I + | 0.1-100 mg/m2 |
| Gemcitabine | 100-3000 mg/m2 |
| Compound of Formula I + | 0.1-100 mg/m2 |
| UFT and optionally + | 50-800 mg/m2 |
| leucovorin | 5-1000 mg/m2 |
| Compound of Formula I + | 0.1-100 mg/m2 |
| Gemcitabine + | 100-3000 mg/m2 |
| Cisplatin | 5-150 mg/m2 |
| Compound of Formula I + | 0.1-100 mg/m2 |
| UFT + | 50-800 mg/m2 |
| Leucovorin | 5-1000 mg/m2 |
| Compound of Formula I + | 0.1-100 mg/m2 |
| Cisplatin + | 5-150 mg/m2 |
| paclitaxel | 40-250 mg/m2 |
| Compound of Formula I + | 0.1-100 mg/m2 |
| Cisplatin + | 5-150 mg/m2 |
| 5FU | 5-5000 mg/m2 |
| Compound of Formula I + | 0.1-100 mg/m2 |
| Oxaliplatin + | 5-200 mg/m2 |
| CPT-11 | 4-400 mg/m2 |
| Compound of Formula I + | 0.1-100 mg/m2 |
| 5FU + | 5-5000 mg/m2 |
| CPT-11 and optionally + | 4-400 mg/m2 |
| leucovorin | 5-1000 mg/m2 |
| Compound of Formula I + | 0.1-100 mg/m2 |
| 5FU + | 5-5000 mg/m2 |
| radiation | 200-8000 cGy |
| Compound of Formula I + | 0.1-100 mg/m2 |
| radiation + | 200-8000 cGy |
| 5FU + | 5-5000 mg/m2 |
| Cisplatin | 5-150 mg/m2 |
| Compound of Formula I + | 0.1-100 mg/m2 |
| Oxaliplatin + | 5-200 mg/m2 |
| 5FU and optionally + | 5-5000 mg/m2 |
| Leucovorin | 5-1000 mg/m2 |
| Compound of Formula I + | 0.1-100 mg/m2 |
| paclitaxel + | 40-250 mg/m2 |
| CPT-11 | 4-400 mg/m2 |
| Compound of Formula I+ | 0.1-100 mg/m2 |
| paclitaxel + | 40-250 mg/m2 |
| 5-FU | 5-5000 mg/m2 |
| Compound of Formula I + | 0.1-100 mg/m2 |
| UFT + | 50-800 mg/m2 |
| CPT-11 and optionally + | 4-400 mg/m2 |
| leucovorin | 5-1000 mg/m2 |

In the above Table I, "5FU" denotes 5-fluorouracil, "Leucovorin" can be employed as leucovorin calcium, "UFT" is a 1:4 molar ratio of tegafur:uracil, and "Epothilone" is preferably a compound described in WO 99/02514 or WO 00/50423, both incorporated by reference herein in their entirety.

While Table I provides exemplary dosage ranges of the Formula I and Formula II compounds and certain anticancer agents of the invention, when formulating the pharmaceutical compositions of the invention the clinician may utilize preferred dosages as warranted by the condition of the patient being treated. For example, Compound 1 may preferably administered at 25-60 mg/m2 every 3 weeks. Compound 2, may preferably be administered at a dosage ranging from 25-500 mg/m2 every three weeks for as long as treatment is required. Preferred dosages for cisplatin are 75-120 mg/m2 administered every three weeks. Preferred dosages for carboplatin are within the range of 200-600 mg/m2 or an AUC of 0.5-8 mg/ml×min; most preferred is an AUC of 4-6 mg/ml×min. When the method employed utilizes radiation, preferred dosages are within the range of 200-6000 cGY. Preferred dosages for CPT-11 are within 100-125 mg/m2, once a week. Preferred dosages for paclitaxel are 130-225 mg/m2 every 21 days. Preferred dosages for gemcitabine are within the range of 80-1500 mg/m2 administered weekly. Preferably UFT is used within a range of 300-400 mg/m2 per day when combined with leucovorin administration. Preferred dosages for leucovorin are 10-600 mg/m2 administered weekly.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired. Intermittent therapy (e.g., one week out of three weeks or three out of four weeks) may also be used.

Certain cancers can be treated effectively with compounds of Formula I and/or Formula II and a plurality of anticancer agents. Such triple and quadruple combinations can provide greater efficacy. When used in such triple and quadruple combinations the dosages set forth above can be utilized. Other such combinations in the above Table I can therefore include "Compound 1" in combination with (1) mitoxantrone+prednisone; (2) doxorubicin+carboplatin; or (3 herceptin+tamoxifen. 5-FU can be replaced by UFT in any of the above combinations.

When employing the methods or compositions of the present invention, other agents used in the modulation of tumor growth or metastasis in a clinical setting, such as antiemetics, can also be administered as desired.

The present invention encompasses a method for the synergistic treatment of cancer wherein a neoplastic agent and a Formula I and/or Formula II compound are administered simultaneously or sequentially. Thus, while a pharmaceutical formulation comprising antineoplastic agent(s) and a Formula I and/or Formula II compound may be advantageous for administering the combination for one particular treatment, prior administration of the anti-neoplastic agent(s) may be advantageous in another treatment. It is also understood that the instant combination of antineoplastic agent(s) and Formula I and/or Formula II compound may be used in conjunction with other methods of treating cancer (preferably cancerous tumors) including, but not limited to, radiation therapy and surgery. It is further understood that a cytostatic or quiescent agent, if any, may be administered sequentially or simultaneously with any or all of the other synergistic therapies.

The combinations of the instant invention may also be co-administered with other well known therapeutic agents that are selected for their particular usefulness against the condition that is being treated. Combinations of the instant invention may alternatively be used sequentially with known pharmaceutically acceptable agent(s) when a multiple combination formulation is inappropriate.

The chemotherapeutic agent(s) and/or radiation therapy can be administered according to therapeutic protocols well known in the art. It will be apparent to those skilled in the art that the administration of the chemotherapeutic agent(s) and/ or radiation therapy can be varied depending on the disease being treated and the known effects of the chemotherapeutic agent(s) and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent(s) or radiation) on the patient, and in view of the observed responses of the disease to the administered therapeutic agents.

In the methods of this invention, a compound of Formula I or Formula II is administered simultaneously or sequentially with an anti-proliferative agent and/or radiation. Thus, it is not necessary that the chemotherapeutic agent(s) and compound of Formula I and/or Formula II, or the radiation and the compound of Formula I and/or Formula II, be administered simultaneously or essentially simultaneously. The advantage of a simultaneous or essentially simultaneous administration is well within the determination of the skilled clinician.

Also, in general, the compound of Formula I and/or Formula II, and chemotherapeutic agent(s) do not have to be administered in the same pharmaceutical composition, and may, because of different physical and chemical characteristics, have to be administered by different routes. For example, the compound of Formula I or II may be administered orally to generate and maintain good blood levels thereof, while the chemotherapeutic agent(s) may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of compound of Formula I and/or II and anti-proliferative cytotoxic agent(s) or radiation will depend upon the diagnosis of the attending physicians and their judgment of the condition of the patient and the appropriate treatment protocol.

If the compound of Formula I and/or Formula II and the anti-neoplastic agent(s) and/or radiation are not administered simultaneously or essentially simultaneously, then the initial order of administration of the compound of Formula I and/or Formula II, and the chemotherapeutic agent(s) and/or radiation, may be varied. Thus, for example, the compound of Formula I and/or II may be administered first followed by the administration of the antiproliferative agent(s) and/or radiation; or the antiproliferative agent(s) and/or radiation may be administered first followed by the administration of the compound of Formula I and/or Formula II. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the anti-neoplastic agent(s) and/or radiation may be administered initially, especially if a cytotoxic agent is employed. The treatment is then continued with the administration of the compound of Formula I and/or II and optionally followed by administration of a cytostatic agent, if desired, until the treatment protocol is complete.

Thus, in accordance with experience and knowledge, the practicing physician can modify each protocol for the administration of a component (therapeutic agent—i.e., compound of Formula I and/or II, anti-neoplastic agent(s), or radiation) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

In order to facilitate a further understanding of the invention, the following examples are presented primarily for the purpose of illustrating more specific details thereof. The scope of the invention should not be deemed limited by the examples, but to encompass the entire subject matter defined by the claims.

Experimental Protocol
Compounds:

The following designations are used to identify the test compounds throughout the examples:

Compound 1: [1S-1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione Compound 2: (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile, hydrochloride salt Compound 3: A CDK inhibitor is shown below

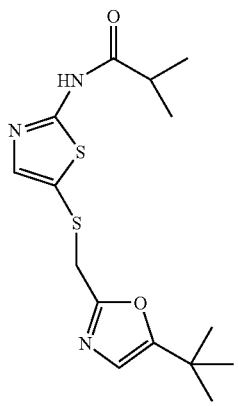 [SMILES: CC(C)C(=O)Nc1ncc(SCc2ncc(C(C)(C)C)o2)s1]

Compound 4: 1S-[1R*,3R*(E),7R*,10S*,11R*,12R*,16S*]]-3-[2-[2-(Aminomethyl)-4-thiazolyl]-1-methylethenyl]-7,11-dihydroxy-8,8,10,12,16-pentamethyl-4,17-dioxabicyclo[14.1.0]heptadecane-5,9-dione.

Compound 5: N-[5-[[[5-(1,1-Dimethylethyl)-2-oxazolyl]methyl]thio]-2-thiazolyl]-4-piperidinecarboxamide.

Chemicals and Solutions:

Unless specified, chemicals and solutions used for the maintenance of cell culture were obtained from GIBCO/BRL. Sterile tissue culture ware was obtained from Corning, N.Y. All other reagents were from Sigma or Fisher at the highest grade available.

Drug Administration:

For administration of Compound 1 (an epothilone) to rodents, two different excipients have been used: (1) ethanol/water (1:9, v/v) and (2) Cremophor®/ethanol/water (1:1:8, v/v). Compound 1 was first dissolved in ethanol or a mixture of Cremophor®/ethanol (50:50). Final dilution to the required dosage strength is made less than 1 h before drug administration. For parenteral administration (IV), dilution was made with water so that the dosing solutions contain the specified excipient composition described above. For oral administration (PO), the dilution was made with 0.25 M sodium phosphate buffer (pH=8.0) at a ratio of 30/70, v/v. Paclitaxel was dissolved in a 50/50 mixture of ethanol and Cremophor® and stored at 4° C.; final dilution of paclitaxel was obtained immediately before drug administration with NaCl 0.9%. The volume of all compounds injected was 0.01 ml/g of mice, and 0.005 ml/g of rats.

Tumor Cell Lines:

HCT116 human carcinoma cell lines and HCT116/VM46 cells, a MDR variant [1], were maintained in McCoy's 5A medium (GIBCO) and 10% heat inactivated fetal bovine serum (GIBCO). A2780 human ovarian carcinoma cells and A2780Tax cells obtained from Dr. Antonio Fojo (NCl, Bethesda, Md.) were maintained in IMEM (GIBCO) and 10% fetal bovine serum (GIBCO). This paclitaxel resistant cell line does not overexpress P-glycoprotein but has point mutations in the M40 isotype of beta-tubulin [2]. Purified tubulin isolated from these resistant cells is refractory to polymerization by paclitaxel and is thought to account for the resistance to this drug, and collateral sensitivity to microtubule depolymerizing agents, such as vinblastine.

Cytotoxicity Assay:

The in vitro cytotoxicity was assessed in tumor cells by a tetrazolium-based colorimetric assay which takes advantage of the metabolic conversion of MTS (3-(4,5-dimethylthiazol-2-yl)-5-(3-carboxymethoxyphenyl)-2-(4-sulphenyl)-2H-tetrazolium, inner salt) to a reduced form that absorbs light at 492 nm [3]. Cells were seeded 24 hr prior to drug addition. Following a 72 hour incubation at 37° C. with serially diluted compound, MTS, in combination with the electron coupling agent phenazine methosulfate, was added to the cells. The incubation was continued for 3 hours, then the absorbency of the medium at 492 nm was measured with a spectrophotometer to obtain the number of surviving cells relative to control populations. The results are expressed as median cytotoxic concentrations (IC50 values).

Clonogenic Cell Colony-formation Assay:

The potency with which Compound 1 and paclitaxel kill clonogenic tumor cells (cells that are able to divide indefinitely to form a colony) in vitro was evaluated by a colony formation assay. The concentration needed to kill clonogenic HCT-116 human colon carcinoma cells by 90% (i.e., the $IC_{90}$) was determined. Analysis of the effects of combination treatment in vitro was by the isobologram and multiplicity methods described by Stephens and Steel [4]

Tubulin Polymerization Assay:

The potency with which Compound 1 and paclitaxel polymerize tubulin isolated from calf brain was evaluated by published technique [5, 6].

Animals:

All rodents were obtained from Harlan Sprague Dawley Co. (Indianapolis, Ind.), and maintained in an ammonia-free environment in a defined and pathogen-free colony. The animal care program of Bristol-Myers Squibb Pharmaceutical Research Institute is fully accredited by the American Association for Accreditation of Laboratory Animal Care (AAALAC).

In Vivo Antitumor Testing:

The following human tumors were used: A2780 ovarian, A2780Tax ovarian (established from cells obtained from Dr. Antonio Fojo, Medicine Branch, NCl, Bethesda, Md.), HCT116/VM46 colon, Pat-7 ovarian (established from a tumor biopsy provided by Dr. Thomas Hamilton, Fox Chase Cancer Center, Philadelphia, Pa.) from a patient who had developed resistance to TAXOL®). The murine fibrosarcoma M5076 was also employed.

The human tumors were maintained in Balb/c nu/nu nude mice. M5076 was maintained in C57BL/6 mice. Tumors were propagated as subcutaneous transplants in the appropriate mouse strain using tumor fragments obtained from donor mice.

The following tumors were passaged in the indicated host strain of mouse: murine M5076 fibrosarcoma (M5076) in C57Bl/6 mice; human A2780 and Pat-7 ovarian carcinomas, HCT116, HCT116/VM46 and LS174T colon carcinoma, Pat-21 breast carcinoma in nude mice. Tumor passage occurred biweekly for murine tumors and approximately every two to eight weeks for the various human tumor lines. With regard to efficacy testing, M5076 tumors were implanted in (C57Bl/6× DBA/2)F1 hybrid mice, and human tumors were implanted in nude mice. All tumor implants for efficacy testing were subcutaneous (sc).

The required number of animals needed to detect a meaningful response were pooled at the start of the experiment and each was given a subcutaneous implant of a tumor fragment (•50 mg) with a 13-gauge trocar. For treatment of early-stage tumors, the animals were again pooled before distribution to the various treatment and control groups. For treatment of animals with advanced-stage disease, tumors were allowed to grow to the pre-determined size window (tumors outside the range were excluded) and animals were evenly distributed to various treatment and control groups. Treatment of each animal was based on individual body weight. Treated animals were checked daily for treatment related toxicity/mortality. Each group of animals was weighed before the initiation of treatment (Wt1) and then again following the last treatment dose (Wt2). The difference in body weight (Wt2−Wt1) provides a measure of treatment-related toxicity.

Tumor response was determined by measurement of tumors with a caliper twice a week, until the tumors reach a predetermined "target" size of 1 gm. Tumor weights (mg) were estimated from the formula:

Tumor weight=(length×width$^2$)÷2

Antitumor activity was evaluated at the maximum tolerated dose (MTD) which is defined as the dose level immediately below which excessive toxicity (i.e. more than one death) occurred. The MTD was frequently equivalent to OD. When death occurs, the day of death was recorded. Treated mice dying prior to having their tumors reach target size were considered to have died from drug toxicity. No control mice died bearing tumors less than target size. Treatment groups with more than one death caused by drug toxicity were considered to have had excessively toxic treatments and their data were not included in the evaluation of a compound's antitumor efficacy.

Tumor response end-point was expressed in terms of tumor growth delay (T−C value), defined as the difference in time (days) required for the treated tumors (T) to reach a predetermined target size compared to those of the control group (C).

To estimate tumor cell kill, the tumor volume doubling time was first calculated with the formula:

TVDT=Median time (days) for control tumors to reach target size−Median time (days) for control tumors to reach half the target size And, Log cell kill=$T-C$÷(3.32×$TVDT$)

Statistical evaluations of data were performed using Gehan's generalized Wilcoxon test [7].

EXAMPLE I

Compound 1 Demonstrates Cytotoxicity Against Cancer Cells In Vitro

Compound 1 has a broad spectrum of activity against a panel of tumor cell lines in vitro. Of the 21 cells lines tested (FIG. 1), 18 have $IC_{50}$ values between 1.4-6 nM. Three cell lines have IC50 values greater than 6 nM: viz. two highly multi-drug resistant (MDR) colon tumor lines HCT116/VM46 (24.5 nM) and MIP (24.8 nM), and the normal mouse lung fibroblast cell line MLF (34.5 nM). It should be noted that Compound 1 did substantially "overcome" the multidrug resistance inherent in these cell lines. Thus, for paclitaxel, the ratios of concentrations (R/S, or resistance ratio) required to inhibit cell growth by 50% in these resistant lines versus those required for the sensitive HCT116 line were 155 and >>55 respectively, for HCT116/VM46 and MIP. In comparison, the R/S ratios for Compound 1 were only 9.4 and 9.5, respectively (Table 2).

TABLE 2

In vitro Cytotoxicity of Compound 1 and Paclitaxel in Paclitaxel-Sensitive and -Resistant Tumor Cell Lines.

| | IC50, nM (resistance ratio) | | |
|---|---|---|---|
| Compound | HCT-116 | HCT116/VM46 | MIP |
| Paclitaxel | 2.1 | 326 (155) | >>112 (>>53) |
| Compound 1 | 2.6 | 24.5 (9.4) | 24.8 (9.5) |

Mechanism of Cytotoxicity—Tubulin Polymerization

The cytotoxic activities of the epothilones, like those of the taxanes, have been linked to stabilization of microtubules which results in mitotic arrest at the G2/M transition. In this regard the potency of Compound 1 is similar to those of its two natural analogs, epothilones A and B (Table 3).

TABLE 3

Tubulin Polymerization Potency of Three Epothilones Relative to Paclitaxel

| Analog | Polymerization Potency, $EC_{0.01}$ (μM) | Ratio of Polymerization Potency of Analog/Paclitaxel |
|---|---|---|
| Compound 1 | 3.5 | 0.4 |
| (Epothilone A) | 2.0 | 0.4 |
| (Epothilone B) | 1.8 | 0.3 |
| Paclitaxel | 8.5, 5.0, 6.0 | 1.0 |

EXAMPLE 2

Compound 1 Inhibits Cell Cycle Progression

Figure 2:
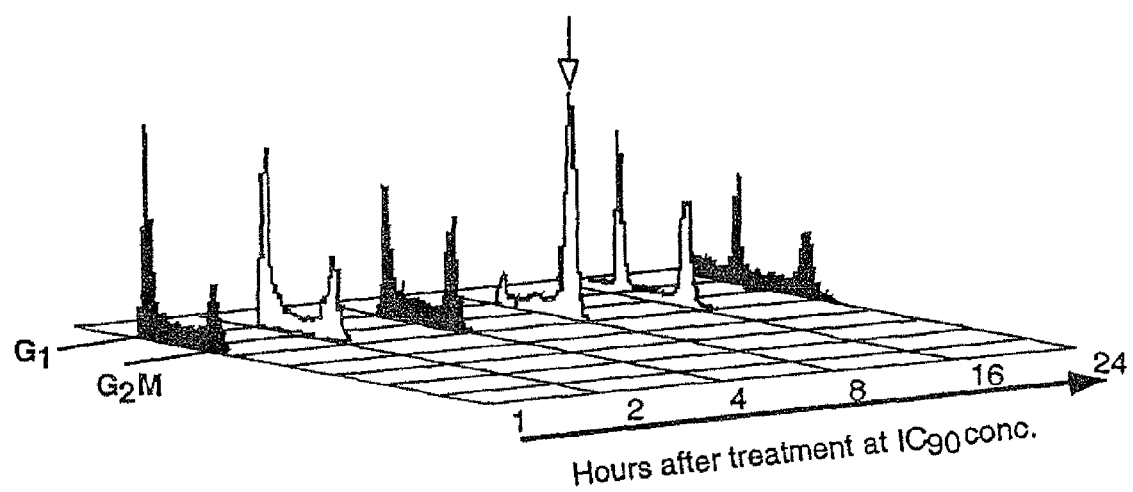
FIG. 2 shows a time course of the mitotic blockade induced by incubation of HCT116 cells in the presence of 7.5 nm Compound 1.

Similar to paclitaxel, Compound 1 blocks cells in the mitotic phase of the cell division cycle. Moreover, the concentration of Compound 1 needed to arrest cells in mitosis corresponds well to the concentration required to kill cells over the same treatment duration. Thus, as shown in FIG. 2, Compound 1 at a concentration close to the IC90 value (•7.5 nM) almost completely blocks cells in mitosis in 8 hours.

EXAMPLE 3

Combination Chemotherapy in vitro

The success of an anticancer agent is dependent not only on its antitumor activity as a single agent but also on its ability to combine successfully with other antineoplastic drugs. Like paclitaxel, Compound 1 induces profound cell cycle perturbation by arresting cells in mitosis. For these reasons, it is particularly pertinent to investigate the behavior of Compound 1 when used in combination chemotherapy. Colony-formation assays were used to examine the cytotoxicity of Compound 1 in combination with several selected anticancer agents of diverse mechanisms of action in vitro.

Figure 3A:
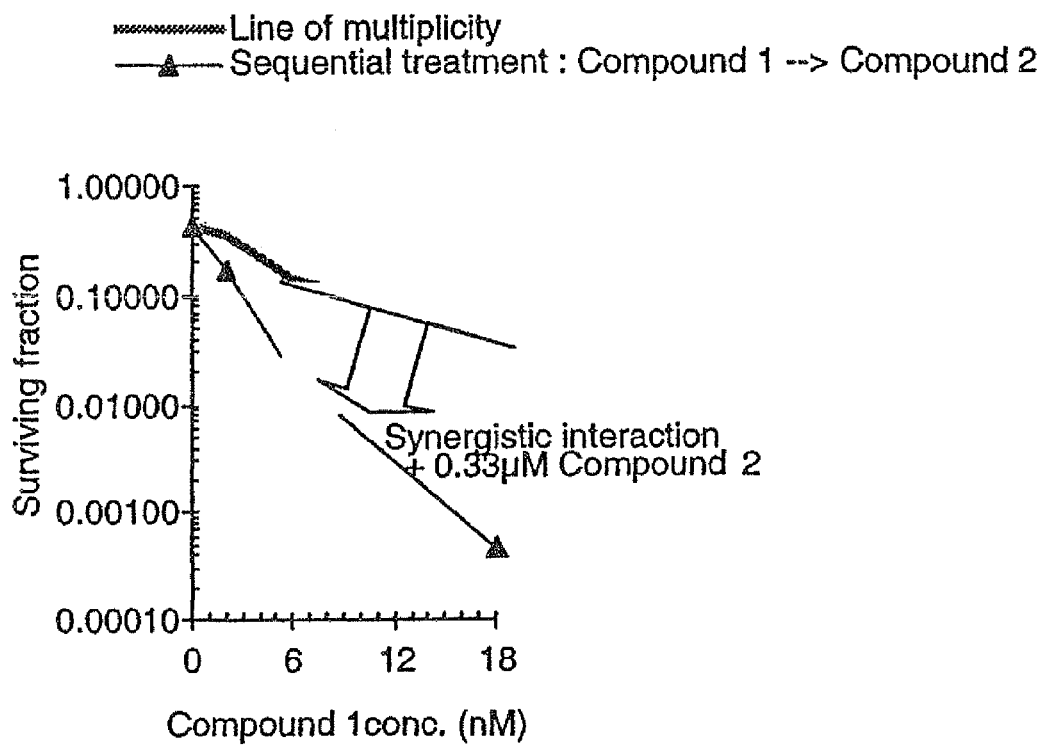
FIGS. 3A and 3B are a pair of graphs showing the synergism with combination chemotherapy using Compound 2 and Compound 1. Synergism was obtained at a range of Compound 1 and Compound 2 concentrations and appeared not to be dependent on a particular concentration of each agent used in the combination. In the case of Compound 2, concentrations of 0.33 µM (FIG. 3A) and 0.11 µM (FIG. 3B) all produced synergistic interaction with various concentrations of Compound 1. In these experiments, Compound 1 was given first for 20 hr followed by Compound 2 for a second 20 hr period of treatment.
Figure 3B:
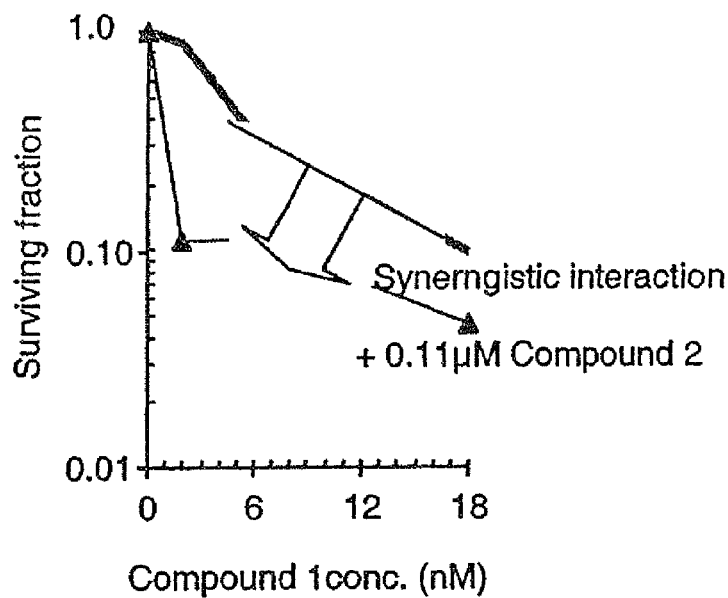

Isobologram analyses showed that the mode of interaction between Compound 1 and other cytotoxic agents in vitro is drug-, sequence- and dose-dependent, and can vary from synergism to antagonism (Table 4). For Compound 2, a ras farnesyl transferase inhibitor currently in Phase I clinical study, synergism was observed when Compound 1 was administered first followed by Compound 2 (FIGS. 3A and 3B). When cells were treated with Compound 1 and Compound 2 simultaneously or in the Compound 2 →Compound 1 sequence, only additivity was observed. With Compound 3, a CDK inhibitor, synergy was again observed when Compound 1 was administered first, but antagonism was observed for the other two treatment sequences.

For paclitaxel, all three treatment sequences resulted in additivity. In the case of cisplatin, additivity was observed when the two agents were used sequentially, but synergism was obtained for simultaneous treatment.

TABLE 4

The effect of sequence of drug exposure on the cytotoxic interaction between Compound 1 and five other antineoplastic agents in the HCT116 human colon carcinoma cell line

| Combination Sequence | Mode of Interaction |
| --- | --- |
| +Compound 2 (ras FT inhibitor) | |
| Compound 1 → Compound 2 | Synergy |
| Compound 2 → Compound 1 | Additivity |
| Simultaneous | Additivity |
| +Compound 3 (CDK inhibitor) | |
| Compound 1 → Compound 3 | Synergy |
| Compound 3 → Compound 1 | Antagonism |
| Simultaneous | Antagonism |
| +Paclitaxel (microtubule stabilizer) | |
| Compound 1 → Paclitaxel | Additivity |
| Paclitaxel → Compound 1 | Additivity |
| Simultaneous | Additivity |
| +Cisplatin (DNA damaging) | |
| Compound 1 → Cisplatin | Additivity |
| Cisplatin → Compound 1 | Additivity |
| Simultaneous | Synergy |

EXAMPLE 4

Antitumor Activity by Parenteral Administration

Compound 1 was evaluated in a panel of eight human and murine tumor models. Five were chosen because of their resistance to paclitaxel (Table 5) and three paclitaxel-sensitive models were included in order to gain a full assessment of the spectrum of antitumor activity of Compound 1.
Paclitaxel-refractory Tumor Models
1. Pat-7 Clinically-derived TAXOL®-resistant Ovarian Carcinoma Model.

This tumor model was established from a tumor biopsy of an ovarian cancer patient (Pat-7), who was initially responsive to TAXOL® treatment but ultimately developed resistance to it following nine courses of monotherapy with TAXOL®. Prior to treatment with TAXOL®, Pat-7 also received numerous other chemotherapeutic agents including carboplatin, cytoxan, VP-16, ifosfamide and altretamine. Tumor biopsy was taken following development of TAXOL® resistance.

Figure 4:
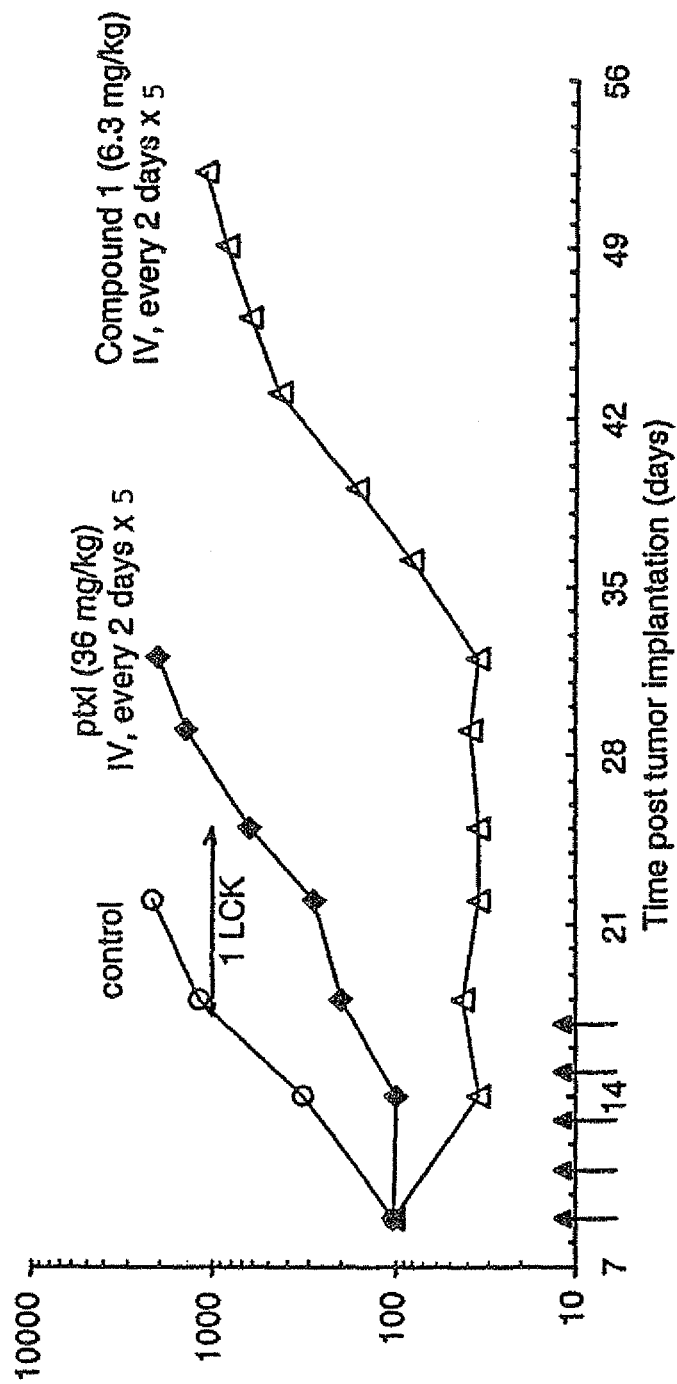
FIG. 4 is a graph showing the comparative anti-tumor activity of Compound 1 and paclitaxel against a scPat-7 human ovarian cancer carcinoma model.

Compound 1 was administered to nude mice bearing staged tumors using an every 2 days×5 schedule. At optimal dose, it was highly active eliciting 2.1 and 4.5 LCKs in two separate tests (Table 6 and FIG. 4). Concomitantly evaluated IV paclitaxel yielded 0.6 and 1.3 LCKs, respectively, at its optimal dose and schedule.

To evaluate the activity of Compound 1 in a second species, Pat-7 was implanted into immunocompromised nude rats and Compound 1 was administered on an IV, every 8 days×2 schedule (Table 6). At the optimal dose of 3 mg/kg/inj, Compound 1 was highly active, yielding 4 of 6 cures. In comparison, paclitaxel produced 2.2 LCK at its optimal dose and no cures (n=6).
2. A2780Tax Human Ovarian Carcinoma Xenograft (Mutated Tubulin).

A2780Tax is a paclitaxel-resistant human ovarian carcinoma model. It was derived from the sensitive parent A2780 line by co-incubation of cells with paclitaxel and verapamil, an MDR-reversal agent. Its resistance mechanism has been shown to be non-MDR related and is attributed to a mutation in the gene encoding the beta-tubulin protein [2].

Compound 1 administered to mice bearing staged tumors on an every 2 days×5 schedule yielded 2.5 LCK at its MTD (6.3 mg/kg/inj). In comparison, IV paclitaxel yielded 0.8 LCK at its MTD. Compound 1 is significantly better than paclitaxel in this test (Table 6).
3. HCT116/VM46 Human Colon Carcinoma Xenograft (Multi-drug Resistant).

HCT116/VM46 is an MDR-resistant colon carcinoma developed from the sensitive HCT116 parent line. In vivo, grown in nude mice, HCT116/VM46 has consistently demonstrated high resistance to paclitaxel (Table 5). In 12 consecutive studies paclitaxel, at its MTD, elicited low LCKs that ranged from 0-0.9 (median=0.35 LCK).

Compound 1 treatment of mice bearing staged HCT116/VM46 tumors using an every 2 days×5 schedule produced significant antitumor effects. At its optimal dose (4.8-6.3 mg/kg/inj) in 3 separate studies, Compound 1 yielded 3.1, 1.3 and 1.8 LCKs. In contrast, concomitantly tested IV paclitaxel yielded 0.4 and 0.7 LCK, respectively, at its MTD in the first two tests.
4. Pat-21, Clinically-derived Paclitaxel Resistant Breast Cancer Model Pat-21 is an early passage paclitaxel-resistant tumor model established from a tumor biopsy of a breast cancer patient with metastatic disease who was given, and failed to respond to, an experimental therapy consisting of 5 cycles of TAXOL® in combination with the multidrug resistance reversal agent dexverapamil. Prior to TAXOL® therapy, the patient also received chemotherapy consisting of adriamycin, cytoxan, methotrexate and 5-FU. Tumor biopsies were obtained after cessation of TAXOL® therapy.

Pat-21 grows at a relative slow rate in nude mice, doubling in volume approximately every 3 weeks. For antitumor efficacy evaluation, two courses of Compound 1 or paclitaxel was administered to mice bearing Pat-21 tumors staged to approximately 100 mg. The two courses were separated by a 3-week interval. Each course consisted of 3 doses given every 4 days. Paclitaxel was completely inactive against this model yielding 0.3 LCK at its MTD of 36 mg/kg/inj. In contrast, Compound 1 was significantly active, currently yielding LCK value of >1.5 LCK at its optimal dose of 10 mg/kg/inj.
5. M5076 Murine Sarcoma Model.

M5076 is a mouse fibrosarcoma that is inherently refractory to paclitaxel in vivo. Compound 1, tested IV on an every 2 days×5 schedule versus unstaged sc tumors, was inactive at its MTD of 8.4 mg/kg/inj, yielding 0.5 and 0.7 LCKs, respectively, in two separate experiments (Table 6). Concomitantly tested IV paclitaxel given by its optimal schedule was also inactive and yielded 0.1 and 0.5 LCK, respectively.

In a separate study, Compound 1 was administered by a less frequent dosing schedule (viz., every 4 days×3) and demonstrated improved antitumor activity, yielding 1.0 LCK at the MTD of 24 mg/kg/inj.

TABLE 5

Tumor Model Characteristics

| Tumor | Histology | Paclitaxel sensitivity | Resistance Mechanism(s) |
|---|---|---|---|
| Human | | | |
| Pat-7 | Ovarian | Resistant[1] | MDR, MRP[2] |
| A2780Tax | Ovarian | Resistant | Tubulin mutation |
| HCT116/VM46 | Colon | Resistant | MDR |
| Pat-21 | Breast | Resistant[1] | Unknown |
| A2780 | Ovarian | Sensitive | — |
| HCT116 | Colon | Sensitive | — |
| LS174T | Colon | Sensitive | — |
| Murine | | | |
| M5076 | Fibrosarcoma | Resistant | Unknown, non-MDR |

[1]Clinical resistance to TAXOL
[2]MRP = multidrug resistance related protein

TABLE 6

Preclinical Antitumor Activity of Compound 1 and Paclitaxel Versus Paclitaxel-Resistant Tumors

| | | | Compound 1 | | |
|---|---|---|---|---|---|
| Tumor | Expt. No. | Rt., schedule | OD[1] (mg/kg) | LCK[2] (cures/ total) | PACLITAXEL LCK[2,3] |
| Human tumors - in nude mice | | | | | |
| Pat-7 | R403 | IV, q2dx5 | 4.8 | 2.1 | 0.6 |
| | 8 | IV, q2dx5 | 6.3 | 4.5 | 1.3 |
| | 12 | IV, q2dx5 | 6.3 | 2.1 | |
| A2780Tax | 12 | IV, q2dx5 | 6.3 | 2.5 | 0.8 |
| HCTVM46 | 32 | IV, q2dx5 | 4.8 | 3.1 | 0.4 |
| | 33 | IV, q2dx5 | 4.8 | 1.3 | 0.7 |
| | 35 | IV, q2dx5 | 6.3 | 1.8 | ND[4] |
| | 35 | IV, q4dx3 | 16 | 2.0 | ND[4] |
| | | Historical paclitaxel responses in 12 consecutive studies | | | (0.4, 0.7, 0.4, 0.3, 0.3, 0.0, 0.2, 0.1, 0.9, 0.9, 0.3, 0.3) |
| Pat-21 | R667 | IV, q4dx3; 41, 68 | 10 | >1.5[5] | 0.3 |
| Human tumors - in nude rats | | | | | |
| Pat-7 | 15 | IV, q8dx2 | 3 | >5 (4/6) | 2.2 (0/6) |
| Murine tumors | | | | | |
| M5076 | 159 | IV, q2dx5 | 8.4 | 0.5 | 0.1 |
| | 162 | IV, q2dx5 | 8.4 | 0.7 | 0.5 |
| | 172 | IV, q4dx3 | 24 | 1.0 | ND |

[1]OD, optimal dose or maximum tolerated dose (MTD).
[2]LCK, gross log cell kill. When 50% or greater of the treated animals are cured, LCK value is calculated based on tumor measurements of the last available date before cure is declared and represents a minimum estimate (>). In such cases, cured rates are also described.
[3]LCK are for optimal dose (dose ranged from 24-36 mg/kg/inj), or highest dose tested if inactive.
[4]ND, not done.
[5]Study still in progress. Interim analysis based on tumor measurement data on the last available date (Jun. 08, 1999) indicates tumor growth delay equivalent to at least 1.5 LCK.

Paclitaxel-sensitive Tumor Models

1. A2780 Human Ovarian Carcinoma Model.

A2780 is a fast-growing human ovarian carcinoma model that is highly sensitive to paclitaxel (Table 6). Nude mice bearing staged tumors were treated with Compound 1 using the "paclitaxel-optimized schedule" of IV administration every 2 days for a total of 5 injections (every 2 days×5). At the maximum tolerated dose (6.3 mg/kg/inj), Compound 1 was highly active yielding >4.8, 2 and 3.1 LCKs in three separate experiments. Concomitantly tested IV paclitaxel, included in the first two studies, yielded 2 and 3.5 LCKs, respectively at its optimal dose.

A2780 grown in nude rats was also utilized. Compound 1, tested at its MTD (1.2 mg/kg/inj), and administered every 2 days×5, was inactive as tested (0.3 LCK). Concomitantly tested IV paclitaxel was highly active, yielding 5 of 7 cures in this study. Subsequent studies in mice with the A2780 tumors has demonstrated that less frequent dosing of Compound 1 is better tolerated and yields improved activity (see Table 6). Thus, the lack of activity in nude rats for Compound 1 may be due to the suboptimum treatment schedule employed. For example, in subsequent studies using the paclitaxel-resistant Pat-7 tumors, Compound 1 was shown to possess significant antitumor activity when administered on a less frequent dosing schedule of every 8 days×2 (Table 6).

2. HCT116 Human Colon Carcinoma Model.

HCT116 is a human colon carcinoma model that has been shown to be highly sensitive to paclitaxel in vivo. Compound 1 administered to nude mice bearing staged (~100 mg) HCT116 tumors was highly active, producing >6.3 LCKs and a large number of cures at three different treatment schedules: every 2 days×5 doses, every 4 days×3 and every 8 days×2 (Table 7). However, these activities though impressive were comparable to but not superior than the historical results obtained for paclitaxel given at its optimal dose and schedule.

3. LS174T.

LS174T is a human colon carcinoma model known to be sensitive to paclitaxel. Compound 1, administered every 4 days×3 produced 2.3 LCKs at its MTD of 16 mg/kg/inj. In comparison, concomitantly tested iv paclitaxel yielded 2.0 LCK at its optimal regimen of 36 mg/kg/inj, administered every 2 days for 5 doses (Table 7).

TABLE 7

Preclinical Antitumor Activity of Compound 1 and Paclitaxel Versus Paclitaxel-Sensitive Tumors

| Tumor | Expt. No. | Rt., schedule | Compound 1 OD[1] (mg/kg) | Compound 1 LCK[2] (Cures/total) | Paclitaxel LCK[2,3] |
|---|---|---|---|---|---|
| Human tumors - in nude mice | | | | | |
| A2780 | 89 | IV, q2dx5 | 6.3 | >4.8 (3/7) | 2 |
| | 92 | IV, q2dx5 | 6.3 | 2 | 3.5 |
| | 111 | IV, q2dx5 | 4.8 | 3.1 | ND[4] |
| | 115 | IV, q2dx5 | 6.3 | 2.4 | ND |
| | 115 | IV, q4dx3 | 16 | >5.3 | ND |
| HCT116 | 52 | IV, q2dx5 | 6.3 | >6.3 (4/8) | ND |
| | 52 | IV, q4dx3 | 10 | >6.3 (5/8) | ND |
| | 52 | IV, q8dx2 | 24 | >6.3 (8/8) | ND |
| LS174T | R578 | IV, q4dx3 | 16 | 2.3 | 2.0 |

[1]OD, optimal dose or maximum tolerated dose (MTD).
[2]LCK, gross log cell kill. When 50% or greater of the treated animals are cured, LCK value is calculated based on tumor measurements of the last date prior to cure is declared and represents a minimum estimate of LCK (>). In such cases, cured rates are also described.
[3]LCK are for optimal dose (dose ranged from 24-36 mg/kg), or highest dose tested if inactive.
[4]ND, not done.

EXAMPLE 5

Antitumor Activity by the Oral Route of Administration

Figure 5A:
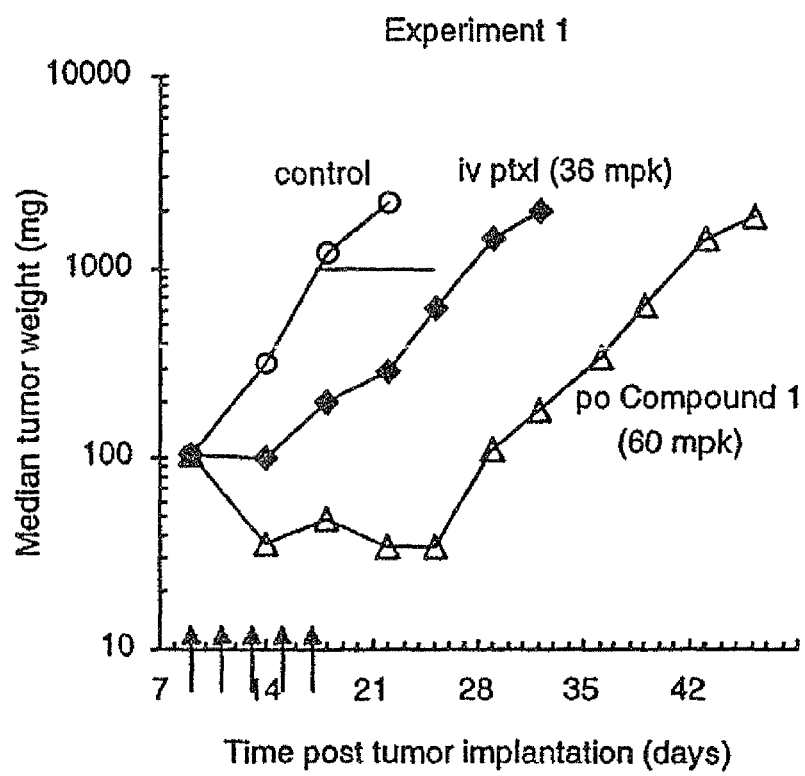
FIGS. 5A and 5B are graphs showing the comparative anti-tumor activity of oral administration of Compound 1 and intravenous administration of paclitaxel in the Pat-7 human ovarian carcinoma model.
Figure 5B:
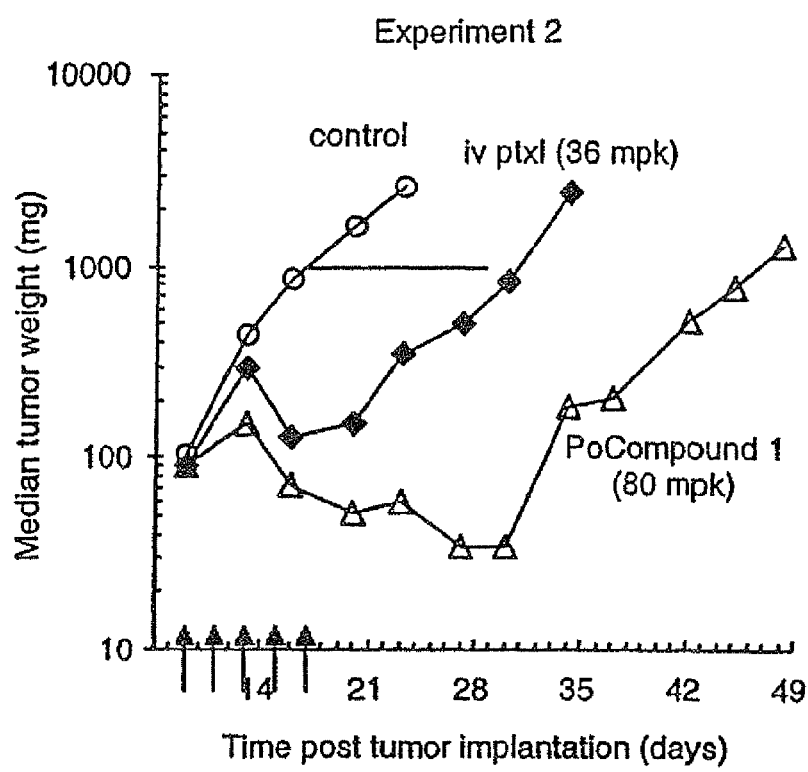

The fact that Compound 1 is significantly more stable at neutral pH than at low pH provided the impetus for the evaluation of Compound 1 by oral administration (PO) in a pH buffering vehicle (0.25M potassium phosphate, pH 8.0). Using an every 2 days×5 schedule, Compound 1 was highly active orally against the Pat-7 human ovarian carcinoma model (Table 8). In two separate experiments oral Compound 1 yielded 3.1 and 2.5 LCKs at its MTD (FIG. 5 and Table 8). In comparison, concomitantly tested IV paclitaxel produced 1.3 and 1.2 LCK, respectively at its optimal dose and schedule.

In the HCT116 human colon carcinoma model, orally administered Compound 1 cured seven of eight mice when administered at a dose of 90 mg/kg/adm, every 2 days for 5 doses. Note that this degree of antitumor activity was equivalent to that achieved by the best concomitantly tested IV regimen (every 8 days×2, see Table 6).

TABLE 8

Antitumor Activity of Oral Compound 1 and IV Paclitaxel

| Tumor | Expt. No. | Rt., schedule | Compound 1 (PO) OD[1] (mg/kg) | Compound 1 (PO) LCK[2] (cures/total) | Paclitaxel (IV) LCK[2,3] |
|---|---|---|---|---|---|
| Pat-7 | 8 | PO, q2dx5 | 60 | 3.1 | 1.3 |
| | 9 | PO, q2dx5 | 80 | 2.5 | 1.2 |
| HCT116 | 52 | PO, q2dx5 | 90 | >6.3 (7/8) | ND[4] |

[1]OD, optimal dose or maximum tolerated dose (MTD).
[2]LCK, gross log cell kill. When 50% or greater of the treated animals are cured, LCK value is calculated based on tumor measurements of the last date prior to cure is declared and represents a minimum estimate of LCK (>). In such cases, cured rates are also described.
[3]LCK are for optimal dose (dose ranged from 24-36 mg/kg), or highest dose tested if inactive.
[4]ND, not done.

Schedule Dependency

Figure 6:
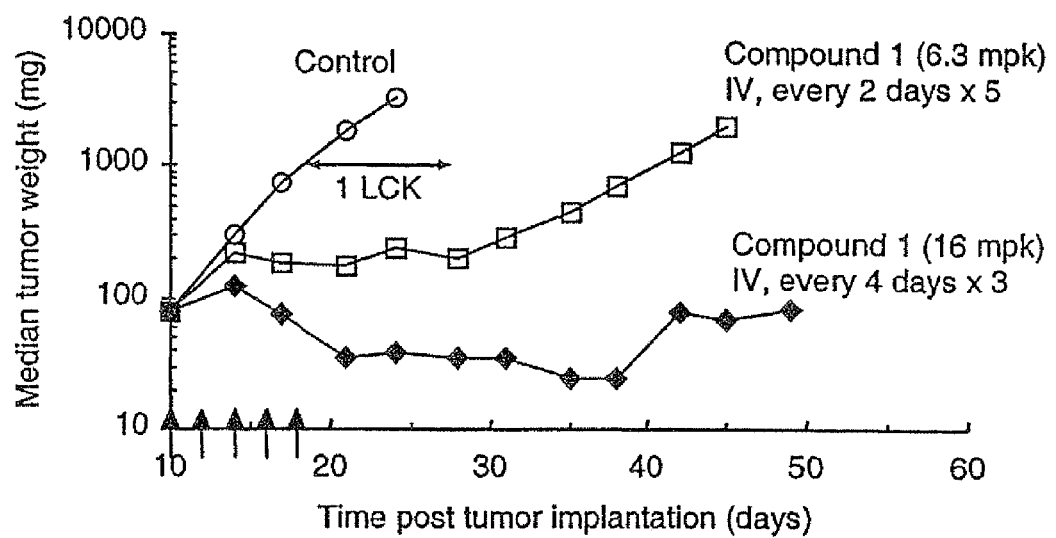
FIG. 6 is a graph showing the dependency of compound 1 anti-tumor activity on treatment schedule in the A2780 human ovarian cancer model.

Several studies were conducted to evaluate the schedule dependency of Compound 1. In the first study, employing the A2780 tumors, Compound 1 was administered to mice by two different schedules: (1) the traditional (optimized for paclitaxel) every 2 days×5 schedule, and (2) the less frequent every 4 days×3 schedule. Although both schedules were active, yielding 2.4 and >5.3 LCKs, respectively, the less frequent dosing schedule allows a higher dose level to be given (MTD=16 mg/kg/inj) and performed far better than the more frequent schedule (MTD=6.3 mg/kg/inj) (FIG. 6 and Table 9).

In a second study, in the HCT116 human colon carcinoma model, three different schedules of treatment were used: q2dx5, q4dx3, as well as q8dx2. All treatments were IV and the tumors were staged to 100 mg at the initiation of treatment. Best results were obtained with the q8dx2 treatment schedule. At the optimal dose of 24 mg/kg/inj, Compound 1 produced 100% cures (8 of 8 mice). The q4dx3 and q2dx5 schedules yielded cures in 5 of 8 and 4 of 8 mice, respectively (Table 9).

In two other studies, employing the Pat-7 and HCT116/VM46 tumors, the efficacy of two IV treatment schedules were compared: q2dx5 and q4dx3. In both cases, the two regimens yielded essentially equivalent antitumor activities (Table 9).

TABLE 9

Schedule-dependency of the antitumor activity of Compound 1

| Tumor | Expt. No. | Rt., schedule | Compound 1 OD[1] (mg/kg) | Compound 1 LCK[2] (cures/total) |
|---|---|---|---|---|
| A2780 | 115 | IV, q2dx5 | 6.3 | 2.4 (0/8) |
| | 115 | IV, q4dx3 | 16 | >5.3 (3/7) |
| HCT116 | 52 | IV, q2dx5 | 6.3 | >6.3 (4/8) |
| | 52 | IV, q4dx3 | 10 | >6.3 (5/8) |
| | 52 | IV, q8dx2 | 24 | >6.3 (8/8) |
| Pat-7 | 12 | IV, q2dx5 | 6.3 | 2.1 |
| | 12 | IV, q4dx3 | 15 | 1.7 |
| HCT116/VM46 | 35 | IV, q2dx5 | 6.3 | 1.8 |
| | 35 | IV, q4dx3 | 16 | 2.0 |

[1]OD, optimal dose or maximum tolerated dose (MTD).
[2]LCK, gross log cell kill. When 50% or greater of the treated animals are cured, LCK value is calculated based on tumor measurements of the last date prior to cure is declared and represents a minimum estimate of LCK (>). In such cases, cured rates are also described.

Compound 1 has clearly demonstrated antitumor activity superior to paclitaxel in five paclitaxel-resistant tumors—four human tumor xenografts and one murine tumor: the clinically-derived paclitaxel resistant Pat-7 ovarian carcinoma; the A2780Tax ovarian carcinoma that is resistant to paclitaxel because of tubulin mutation; the HCT116/VM46 MDR colon carcinoma, the clinically-derived paclitaxel-resistant Pat-21 breast carcinoma; and the murine fibrosarcoma M5076. Against three paclitaxel-sensitive human tumor xenografts Compound 1 produced antitumor activity equivalent to paclitaxel: A2780 human ovarian carcinoma; HCT116 and LS174T human colon carcinoma. In addition, Compound 1 is orally active, producing antitumor activity by the oral route that is equivalent to that produced by IV drug administration in two different human tumor xenografts.

EXAMPLE 6

Figure 7:
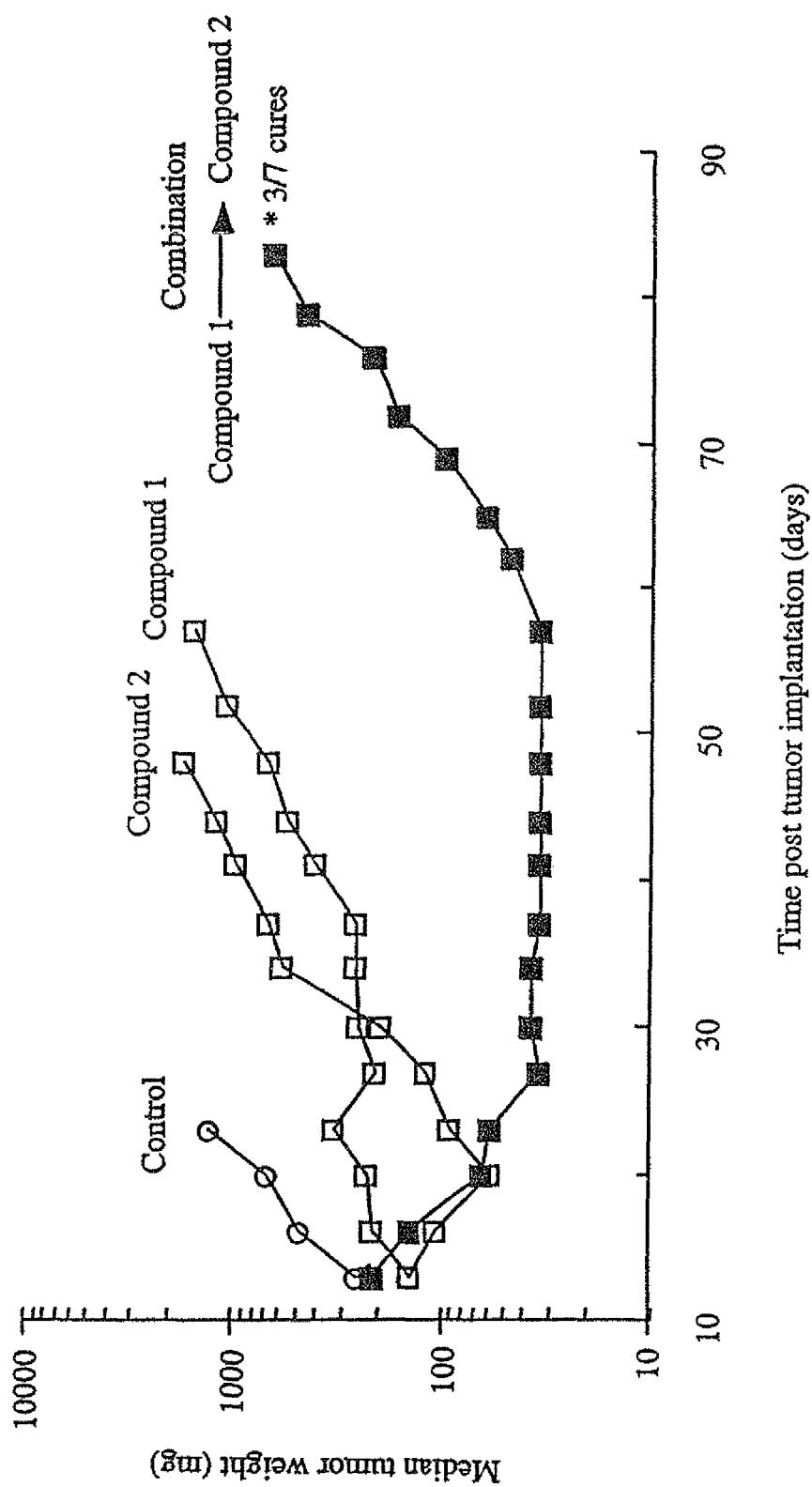
FIG. 7 is a graph demonstrating the therapeutic synergism in vivo in multidrug-resistant human tumor xenografts (HCTVM46 human colon carcinoma) grown in nude mice following combination chemotherapy using Compound 2 and Compound 1. Compound 1 was administered iv 24 hr preceding the administration Compound 2 ip. Data shown were maximum tolerated regimens: Compound 1 alone (15 mg/kg, q4dx3), Compound 2 alone (400 mg/kg, q4dx3), combination (Compound 1 at 6 mg/kg followed by Compound 2 at 400 mg/kg).

Anti-proliferative Agents in Combination with the Compounds of the Invention Act Synergistically to Kill Tumor Cells in Human Tumor Xenografts Therapeutic synergism was also clearly demonstrated with the combination of Compound 1 and Compound 2 in vivo in the multidrug resistant human colon carcinoma xenografts HCT/VM46. Both Compound 1 and Compound 2 have modest antitumor activity in this model as a single agent treatment (FIG. 7). Both agents caused greater than 1 LCK of tumor response (1.6 and 1.1 LCK, respectively) but did not induce tumor cure. However, when the two agents were administered in combination (Compound 1 followed 24 hr later with Compound 2), dramatic improvement in antitumor activity was observed. Notably, a highly significant increase in tumor growth delay (3.7 LCK) including enhanced curative effects were observed in 3 out of 7 mice (FIG. 7).

Figure 8:
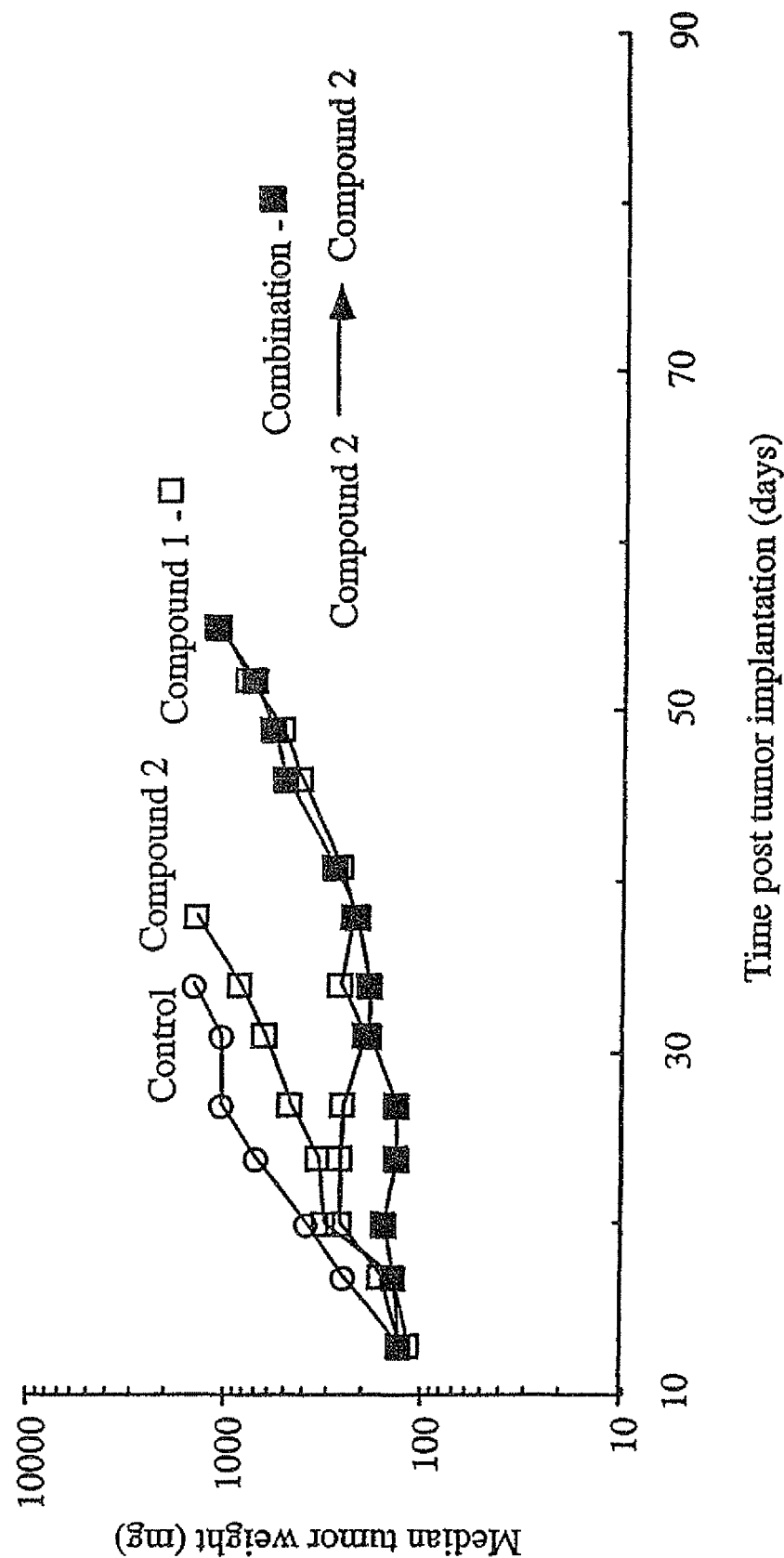
FIG. 8 demonstrates the schedule dependency of combining Compound 1 and Compound 2 in vivo against a multidrug-resistant human tumor xenografts (HCTVM46 human colon carcinoma) grown in nude mice. In contrast to other reported schedules described above, administration of Compound 2 one day before Compound 1 did not result in therapeutic synergism. Data shown were maximum tolerated regimens: Compound 1 alone (10 mg/kg, iv, q4dx3), Compound 2 alone (400 mg/kg, ip, q4dx3), combination (Compound 2 at 300 mg/kg followed by Compound 1 at 10 mg/kg).

The sequence dependency of the combination was demonstrated. When Compound 2 treatment was administered 24 h prior to Compound 1, no therapeutic synergism was observed (FIG. 8), with the combination performing only as well as Compound 1 given alone.

EXAMPLE 7

Pharmacological Studies of Compound 1 Alone and in Combination with Other Anti-neoplastic Agents in Patients with Advanced Cancer Given the cytotoxic effects of Compound 1 both in vivo and in vitro, phase I clinical trials are underway to assess toxicity in patients with advanced cancer. Patients having peritoneal ovarian cancer, non-small cell lung carcinoma, melanoma and an unknown primary cancer were assessed for an objective response. Compound 1 was given in escalating doses which ranged from 7.4 mg/m2 to 65 mg/m2. These studies revealed the MTD. The dose recommended for Phase II clinical trials is 50 mg/m2 using q3 week schedule.

Compound 1 is also being assessed in Phase I studies in combination with other chemotherapeutic agents. Compound 1 will be administered at a starting dose of 30 mg/m2 in combination with carboplatin at 6 AUC using q3 week schedule. Other studies are being performed to assess the efficacy of combined administration of Compound 1 at 30 mg/m2 and doxorubicin at 50 mg/m2 using a q3 week schedule. Combination chemotherapeutic regimens wherein Compound 1 at 30 mg/m2 is combined with CPT-11 at 150 mg/m2 are also underway.

Compound 1 is also being assessed in Phase II clinical studies on cancer patients who have not responded to treatment regimens using taxanes, anthracyclines, platinum, and 5 FU in combination with CPT-11. In these studies, Compound 1 will be administered using a dosing regimen consisting of 50/mg/m2 intravenous infusion for 1 hour every three weeks for 18 cycles (PR and SD) or 4 cycles after CR.

REFERENCES

1. Long B H, et al., Mechanisms of resistance to etoposide and teniposide in acquired resistant human colon and lung carcinoma cell lines. Cancer Research, 1991. 51: 5275-5284.
2. Giannakakou P, et al., Paclitaxel-resistant human ovarian cancer cells have mutant beta-tubulins that exhibit impaired paclitaxel-driven polymerization. J. Biol. Chem., 1997. 272(27): 17118-25.
3. Riss T L, et al. Comparison of MTT, XTT, and a novel tetrazolium compound MTS for in vitro proliferation and chemosensitivity assays. Molecular Biology of the Cell, 1992. 3 (suppl.): 184a.
4. Stephens T C, Steel G G. The evaluation of combinations of cytotoxic drugs and radiation: Isobolograms and therapeutic synergism. In, Rodent tumor models in experimental cancer therapy, pp. 248. Ed. Robert F. Kallman. Pergamon Press, NY.
5. Long B H, Fairchild C R. Paclitaxel inhibits progression of mitotic cells to G(1) phase by interference with spindle formation without affecting other microtubule functions during anaphase and telophase. Cancer Research, 1994. 54(16): 4355-4361.
6. Williams, R C, Lee, J C. Preparation of tubulin from brain. Methods in Enzymology, 1982. 85(Part D): 376-385.
7. Gehan, G A. A generalized Wilcoxon test for comparing arbitrarily singly-censored samples. Biometrika, 1985. 2: 203-233.

The present invention is not limited to the embodiments specifically described above, but is capable of variation and modification without departure from the scope of the appended claims.

What is claimed is:

1. A method for treating cancer selected from metastatic breast cancer, lung cancer, pancreatic cancer, ovarian cancer, prostate cancer, colon cancer, and small cell lung cancer, which comprises administering to a mammal a combination therapy comprising a dosage unit of Compound (1), having the formula,

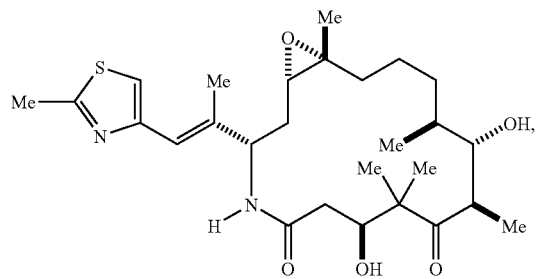

or a stereoisomer of Compound (1), and a dosage unit of bevacizumab, wherein the combination therapy will provide a greater anti-cancer effect than the effect obtainable with either the dosage unit of Compound (1) or bevacizumab alone.

2. The method of claim 1 wherein the cancer is refractory, resistant, or sensitive to taxane treatment.

3. The method of claim 1, wherein bevacizumab is administered following the administration of Compound (1).

4. The method according to claim 1, wherein bevacizumab is administered before the administration of Compound (1).

5. The method according to claim 1, wherein bevacizumab is administered substantially simultaneously with the administration of Compound (1).

* * * * *

UNITED STATES PATENT AND TRADEMARK OFFICE
CERTIFICATE OF CORRECTION

PATENT NO.        : 8,598,215 B2                    Page 1 of 1
APPLICATION NO.   : 12/508100
DATED             : December 3, 2013
INVENTOR(S)       : Francis Y. F. Lee It is certified that error appears in the above-identified patent and that said Letters Patent is hereby corrected as shown below:

On the Title Page:

Item (56), References Cited, under OTHER PUBLICATIONS:

Page 2, Column 1, BisSery, M.-C. et al. reference, line 1, change "BisSery" to -- Bissery --.

Page 2, Column 1, Fujisawa, T. et al. reference, line 2, change "FeCI$_3$" to -- FeCl$_3$ --.

Signed and Sealed this
Twenty-fourth Day of March, 2015

Michelle K. Lee
*Director of the United States Patent and Trademark Office*